Figure 1:
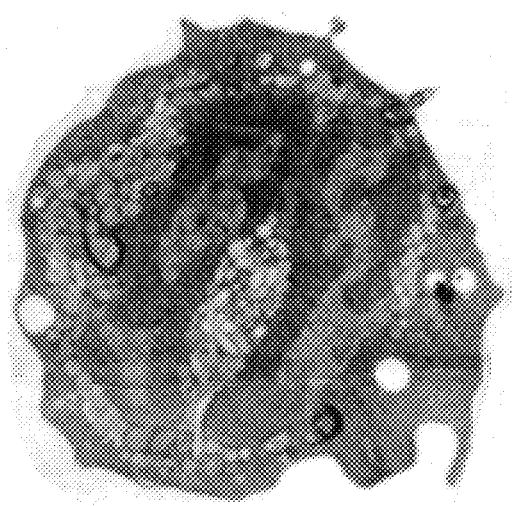

US005772994A

United States Patent [19]
Ildstad et al.

[11] Patent Number: 5,772,994
[45] Date of Patent: Jun. 30, 1998

[54] HEMATOPOIETIC FACILITATORY CELLS AND THEIR USES

[75] Inventors: Suzanne T. Ildstad; Richard L. Simmons, both of Pittsburgh, Pa.; Camillo Ricordi, Miami Beach, Fla.; Sherry M. Wren, Pittsburgh; Christina Kaufman, Munhall, both of Pa.

[73] Assignee: The University of Pittsburgh, Pittsburgh, Pa.

[21] Appl. No.: 463,908

[22] Filed: Jun. 5, 1995

Related U.S. Application Data

[63] Continuation of Ser. No. 69,315, May 28, 1993, abandoned.

[51] Int. Cl.$^6$ ............................ A01N 63/00; C12N 15/00
[52] U.S. Cl. ........................ 424/93.7; 424/93.71; 435/2; 435/724; 435/355; 435/372
[58] Field of Search ................................ 424/93.7, 93.71, 424/529, 537; 435/2, 7.24, 240.1–240.2, 352, 353, 354, 355, 363, 366, 372

[56] References Cited

U.S. PATENT DOCUMENTS

| | | |
|---|---|---|
| 5,061,620 | 10/1991 | Tsukamoto et al. . |
| 5,087,570 | 2/1992 | Weissmann et al. . |
| 5,130,144 | 7/1992 | Civin . |
| 5,192,553 | 3/1993 | Boyse et al. . |

FOREIGN PATENT DOCUMENTS

| | | | |
|---|---|---|---|
| 0451611 | 3/1991 | European Pat. Off. | .......... C12N 5/08 |
| 93/09234 | 5/1996 | WIPO . | |

OTHER PUBLICATIONS

Kaufman et al. Blood 82: 456A (1993).
Kaufman et al. J. Immunol. 150: 321 A (1993).
Colson et al. J. Cell Biochem. Suppl. 18: A106 (1994).
Kaufman et al. J. Cell Biochem. Suppl. 18: A112 (1994).
Auchincloss et al. Paul (Ed) Fundamental Immunology, Raven Press, 1989 pp. 889–922.
Palathumpat et al., 1992, *Journal of Immunology*, 148(2):373–380.
Ildstad et al., 1991, *The Journal of Experimental Medicine*, 174:467–478.
Ildstad et al., 1992, *The Journal of Experimental Medicine*, 175:147–155.
Ricordi et al., 1992, *Lancet*, 339:1610–1611.
Aksentijevich et al., 1992, *Transplantation*, 53(5):1108–1114.
Lapidot et al., 1992, *Blood*, 80(9): 2406–2411.
Sykes, Megan, 1990, "Unusual T Cell Populations in Adult Murine Bone Marrow," *J. Immunol.* 145(10):3209–3215.
Bruley–Rosset et al., 1990, "MIs Generated Suppressor Cells," *J. Immunol.* 145(12):4046–4052.
Caldwell, 1992, "The transplanted self," Discover, pp. 62–68.
Wren et al., 1992, "Rabbit anti mouse brain is not a T cell depleting agent," Keystone Symposia on Molecular and Cellular Biology in Keystone, Colorado, Jan. 1992, (Abstract).

van den Brink et al., 1991, "Cross–species mixed chimerism (mouse+rat→mouse): Facilitated engraftment of rat stem cells with untreated rat bone marrow," Transplant. Proc. 23(1):807–808.
Wood et al., 1991, "CD45 epitope mapping of human CD1a$^+$ dendritic cells and peripheral blood dendritic cells," Amer. J. Pathol. 138(6):1451–1459.
Lapidot et al., 1990, "Enhancement of bone marrow allografts from nude mice into mismatched recipients by T cells void of graft–versus–host activity," Proc. Natl. Acad. Sci. USA 87:4595–4599.
Sykes et al., 1989, "Effects of T cell depletion in radiation bone marrow chimeras," J. Immunol. 143(11):3503–3511.
Sykes et al., 1988, "Effects of T cell depletion in radiation bone marrow chimeras," J. Immunol. 141(7):2282–2288.
Blazar et al., 1988, "Absence of a facilitory role for NK 1.1–positive donor cells in engraftment across a major histocompatibility barrier in mice," Transplant. 45(5):876–883.
Ferrara et al., 1987, "Engraftment following T–cell–depleted marrow transplantation," Transplant. 43(4):461–467.
Martin et al., 1987, "Human marrow transplantation: An immunological perspective," Advances in Immunol. 40:379–439.
Ildstad et al., 1986, "Effect of selective T cell depletions in mixed xenogeneic reconstitution on specific hyporeactivity to transplantation across a species barrier," Transplant. 41(3):372–376.
Ildstad et al., 1986, "Effect of selective T cell depletion of host and/or donor bone marrow on lymphopoietic repopulation, tolerance, and graft–vs–host disease in mixed allogeneic chimeras (B10+B10.D2→B10)," J. Immunol. 136(1):28–33.

(List continued on next page.)

*Primary Examiner*—Lila Feisee
*Assistant Examiner*—Phillip Gambel
*Attorney, Agent, or Firm*—Pennie & Edmonds LLP

[57] ABSTRACT

The present invention relates to mammalian hematopoietic facilitatory cells (FC). In particular, it relates to the isolation, characterization and uses of the FC. The FC of the present invention can be distinguished from all other known bone marrow cells by their morphology, cell surface phenotype and in vivo function. It has now been established that purified hematopoietic stem cells alone or bone marrow cells depleted of FC do not readily engraft in a recipient. When co-administered with other bone marrow cells, especially the hematopoietic stem cells into a recipient, the FC enhance their engraftment, without apparent adverse biologic activities. In fact, the ability of the FC to enhance the engraftment of bone marrow cells in esablishing lymphohematopoietic chimerism without producing graft versus host disease also induces donor-specific tolerance to permit the permanent acceptance of donor's cells, tissues and organs. Therefore, FC may have a wide range of applications, including, but not limited to, hematopoietic reconstitution by bone marrow transplantation for the treatment of cancers, anemias, autoimmunity, immunodeficiency, viral infections and metabolic disorders as well as facilitation of solid organ, tissue and cellular transplantation.

72 Claims, 1 Drawing Sheet

OTHER PUBLICATIONS

Vallera et al., 1982, "Bone marrow transplantation across major histocompatibility barriers in mice," Transplant. 33(3):243–248.

Vallera et al., 1982, "Bone marrow transplantation across major histocompatibility barriers in mice," J. Immunol. 128(2):871–875.

Sharkis et al., 1979, "Genetic requirements for bone marrow transplantation for stem–cell–defective W/W$^v$ mice," Transplant. Proc. XI(1):511–516.

Wiktor–Jedrzejczak et al., 1977, "Theta–sensitive cell and erythropoiesis: Identification of a defect in W/W$^v$ anemic mice," Science 196:313–315.

Reisner et al. Blood 61: 341–348 (1983).

Rice et al. Stem Cells 11: 326–335 (1993).

Cowan et al. J. Clinical Immunology 5:370–376 (1985).

Yu et al. J. Surgical Research 48: 517–522 (1990).

Chatewoud et al. Transplantation 55: 443–445 (1993).

Beelew Cancer Immunol. Immunother. 34: 97–102 (1991).

Maeda et al. J Immunol. 153: 4311–4320 (1994).

Beelen et al. Onkologie 11: 56–58 (1988).

Szilvassy et al. PNAS 87: 8736–8740 (1990).

Szilvassy et al. Blood 74: 930–939 (1989).

Lerner et al. Exp. Hematol. 18:114–118 (1990).

Frame et al. Transplantation 47: 984–988 (1989).

Gee et al. Bone Marrow Transplantation 2: 155–163 (1987).

Vartdal et al. Bone Marrow Transplantation 2 (Suppl 2) 94–98 (1987).

Mitsuyasu et al. Annals Internal Med. 105: 20–26 (1986).

HEMATOPOIETIC FACILITATORY CELLS AND THEIR USES

This is a continuation of application Ser. No. 08/069,315, filed May 28, 1993, now abandoned.

This invention was made, in part, with government support under R01 AI-30615 awarded by the National Institutes of Health. The government has certain rights in the invention.

1. INTRODUCTION

The present invention relates to mammalian hematopoietic facilitatory cells (FC). In particular, it relates to the isolation, characterization and uses of the FC. The FC of the present invention can be distinguished from all other known bone marrow cells by their morphology, cell surface phenotype and in vivo function. It has now been established that purified hematopoietic stem cells alone or bone marrow cells depleted of FC do not readily engraft in a recipient. When co-administered with other bone marrow cells, especially the hematopoietic stem cells into a recipient, the FC enhance their engraftment, without apparent adverse biologic activities. In fact, the ability of the FC to enhance the engraftment of bone marrow cells in esablishing lymphohematopoietic chimerism without producing graft versus host disease also induces donor-specific tolerance to permit the permanent acceptance of donor's cells, tissues and organs. Therefore, FC may have a wide range of applications, including, but not limited to, hematopoietic reconstitution by bone marrow transplantation for the treatment of cancers, anemias, autoimmunity, immunodeficiency, viral infections and metabolic disorders as well as facilitation of solid organ, tissue and cellular transplantation.

2. BACKGROUND OF THE INVENTION

A major goal in solid organ transplantation is the engraftment of the donor organ without a graft rejection immune response generated by the recipient, while preserving the immunocompetence of the recipient against other foreign antigens. Typically, nonspecific immunosuppressive agents such as cyclosporine, methotrexate, steroids and FK506 are used to prevent host rejection responses. They must be administered on a daily basis and if stopped, graft rejection usually results. However, nonspecific immunosuppressive agents function by suppressing all aspects of the immune response, thereby greatly increasing a recipient's susceptibility to infections and diseases, including cancer. Furthermore, despite the use of immunosuppressive agents, graft rejection still remains a major source of morbidity and mortality in human organ transplantation. Only 50% of heart transplants survive 5 years and 20% of kidney transplants survive 10 years. (See Powles, 1980, Lancet, p. 327; Ramsay, 1982, New Engl. J. Med., p. 392). Most human transplants fail within 10 years without permanent acceptance. It would therefore be a major advance if tolerance can be induced in the recipient.

The only known clinical condition in which complete systemic donor-specific transplantation tolerance occurs is when chimerism is created through bone marrow transplantation. (See Qin et al., 1989, J. Exp. Med. 169:779; Sykes et al., 1988, Immunol. Today 9:23; Sharabi et al., 1989, J. Exp. Med. 169:493). This has been achieved in neonatal and adult animal models as well as in humans by total lymphoid irradiation of a recipient followed by bone marrow transplantation with donor cells. The success rate of bone marrow transplantation is, in part, dependent on the ability to closely match the major histocompatibility complex (MHC) of the donor cells with that of the recipient cells. The MHC is a gene complex that encodes a large array of individually unique glycoproteins expressed on the surface of both donor and host cells that are the major targets of transplantation rejection immune responses. In the human, the MHC is referred to as HLA. When HLA identity is achieved by matching a patient with a family member such as a sibling, the probability of a successful outcome is relatively high, although graft-versus-host disease (GVHD) is still not completely eliminated. However, when allogeneic bone marrow transplantation is performed between two MHC-mismatched individuals of the same species, common complications involve failure of engraftment, poor immunocompetence and a high incidence of GVHD.

GVHD is a potentially lethal complication in bone marrow transplantation, which occurs in about 35–50% of recipients of untreated HLA-identical marrow grafts (Martin et al., 1985, Blood 66:664) and up to 80% of recipients of HLA-mismatched marrow. Unfortunately, only 30% of patients generally have a suitably matched HLA-identical family member donor, and thus most patients are either excluded from being considered for bone marrow transplantation, or if they are transplanted must tolerate a high risk of GVHD. GVHD results from the ability of immunocompetent mature immune cells (mainly T cells, but some B cells and natural killer cells) in the donor graft to recognize host tissue antigens as foreign and invoke an adverse immunologic reaction. Although mixed allogeneic reconstitution, in which a mixture of donor and recipient marrow is transplanted, results in improved immunocompetence and increased resistance to GVHD, successful engraftment is still not consistently achieved and GVHD still often occurs.

Recent studies in bone marrow transplantation suggest that the major cause of GVHD are T-cells, as the removal of T cells from the donor cell preparation was associated with a reduction in the incidence of GVHD. (Vallera et al., 1989, Transplant, 47:751; Rayfield, 1984, Eur. J. Immunol., P. 308; Vallera, 1982, J. Immunol., 128:871; Martin and Korngold, 1978, J. Exp. Med., p 1687; Prentice, 1984, Lancet P. 472). After T-cells were implicated to be the predominant mediator of GVHD in animal models, aggressive protocols for T-cell depletion (TCD) of human donor bone marrow were instituted. Although the incidence of GVHD was decreased dramatically, TCD was accompanied by a significant increase in the failure of engraftment, indicating that T cells might also play a positive role in bone marrow engraftment. (Soderling, J. Immunol., 1985, 135:941; Vallera, 1982, Transplant. 33:243; Pierce, 1989, Transplant., p. 289). The increase in failure of engraftment in human recipients ranged from about 5–70% of total patients and was related to the degree of MHC disparity between the donor and recipient (Blazar, 1987, UCLA Symp., p. 382; Filipovich, 1987, Transplant., p. 62; Martin et al., 1985, Blood 66:664; Martin et al., 1988, Adv. Immunol. 40:379). Patients with failed engraftment usually die even if a second bone marrow transplant is performed. Consequently, most transplant institutions in the United States have abandoned TCD of donor bone marrow and, thus, must tolerate a high level of GVHD which leads to significant morbidity and mortality. Thus, the application of bone marrow transplantation as a form of treatment is limited only to settings where the potential of GVHD is clearly outweighed by the potential benefit.

The implication that T cells might participate in both harmful GVHD reactions and helpful engraftment facilitation was an enigma that existed for a long time in the scientific community. Investigators began to search for the possible existence of a bone marrow component which could facilitate bone marrow engraftment but was removed during TCD. Identification and purification of this facilitating component would potentially allow the design of transplant protocols to selectively prevent GVHD, while preserving the cells that can enhance engraftment.

Although most investigators speculated that the facilitating component was a hematopoietic cell distinct from the hematopoietic stem cells, such a component had never been identified or characterized prior to the present invention. In fact, all evidence pointed towards the involvement of some form of T cells. There remained a desperate need for the precise knowledge of the identity of this component which might facilitate engraftment of hematopoietic stem cells in a recipient without producing GVHD.

3. SUMMARY OF THE INVENTION

The present invention satisfies the above-described long-felt need. The present invention relates to mammalian hematopoietic FC, methods of isolating the cells, and methods of using the cells for facilitating reconstitution of a damaged or destroyed autologous, syngeneic, allogeneic or xenogeneic hematopoietic system with stem cells as well as for inducing donor-specific tolerance for the transplantation of donor cells, tissues and solid organs.

The invention is based, in part, on the Applicants' discovery that the murine bone marrow contains a population of cells displaying a phenotype of $THY1^+$, MHC Class $II^+$ (only dim to intermediate levels of expression), $CD45^+$, $CD45R^+$, $CD8^+$, $CD3^+$ and $\alpha\beta$ $TCR^-$ which are capable of facilitating allogeneic donor bone marrow cell engraftment in a recipient. Both negative selection procedures involving the removal of these cells and positive selection methods involving the addition of these cells in highly purified or partially purified form confirm that they possess engraftment-facilitating activities and are distinguishable from the T cells responsible for GVHD. Morphologically, purified FC are distinct from all other hematopoietic cell types, including lymphocytes. Furthermore, these cells function in a MHC-specific fashion in that optimal engraftment of bone marrow cells is achieved if they are of the same MHC haplotype as the FC. The FC of the invention can also mediate xenogeneic bone marrow engraftment across species barriers in establishing mixed lymphohematopoietic chimerism.

The invention is described by way of examples in which mouse, rat, baboon, and human FC are isolated, and their cell surface phenotype is characterized. Isolated FC are used to successfully establish engraftment of donor bone marrow cells without the manifestation of GVHD. Additionally, donor bone marrow cells depleted of GVHD-producing cells, particularly T cells, with the retention of FC, also produce engraftment and mixed chimerism, rendering the recipient immunologically tolerant to the donor. A wide variety of uses for the FC are encompassed by the invention described herein, including, but not limited to, transplantation, and treatment of cancer, metabolic disorders, immunodeficiency, autoimmunity, diabetes, hemoglobinopathies, hepatitis, AIDS and aging.

The present invention provides for methods of purifying FC from bone marrow or other physiological sources of hematopoietic cells. The FC are purified by separations based on the presence or absence of specific markers.

By utilizing the ability of the FC to facilitate engraftment of bone marrow or purified stem cells and thus establish a chimeric hematopoietic immune system, the present invention provides for methods of transplantation which confer donor-specific transplantation tolerance and eliminate the need for nonspecific immunosuppressive agents.

It is an object of the present invention to provide a cellular composition comprising purified or partially purified hematopoietic FC.

It is a further object of the present invention to provide a cellular composition comprising purified or partially purified hematopoietic FC and purified or partially purified hematopoietic stem cells which are MHC-specific to the FC.

It is a further object of the present invention to provide a cellular composition comprising purified or partially purified hematopoietic FC, hematopoietic stem cells which are MHC-specific to the FC, and one or more additional hematopoietic cell components which are MHC-specific to the FC.

It is a further object of the present invention to provide a cellular composition comprising hematopoietic FC and hematopoietic stem cells in which only T cells responsible for GVHD have been specifically and selectively removed.

It is another object of the present invention to provide methods of purifying hematopoietic FC from physiological sources of hematopoietic cells.

It is another object of the present invention to provide methods of establishing a mixed allogeneic, mixed xenogeneic, completely allogeneic, and completely xenogeneic chimeric immune system in a recipient.

It is another object of the present invention to provide methods of transplanting a donor physiological component into a recipient which allows for donor specific transplantation tolerance.

It is another object of the present invention to provide methods of treating a variety of diseases and disorders by bone marrow transplantation involving FC.

3.1. DEFINITIONS

As used herein, "recipient" means any mammal, including humans.

As used herein, "donor" means any mammal, including humans.

As used herein, except where its traditionally understood meaning is explicitly referred to, "MHC-specific" cells means cells whose major histocompatibility complex does not prevent the facilitatory cell from facilitating engraftment, whether the cells major histocompatibility complex is actually identical to the facilitatory cell or, in the case of a universal facilitatory cell, simply not a barrier to engraftment.

As used herein, "purified" means any enrichment or increase in concentration of specified cells from their natural state including isolation of those cells.

As used herein, "substantially destroy" means to destroy all or almost all of a recipient's immune system.

As used herein, "lethally irradiate" means to substantially destroy a recipient's immune system with radiation.

As used herein, "immunosuppress" means to suppress the functions of a recipient's immune system, including suppression of the propensity to attack foreign-recognized cells (i.e., rejection of a graft).

As used herein, "cytoreduce" means to destroy a portion of the cells of the recipient's immune system so as to make physical space for administered immune cells.

As used herein, "donor physiological component" means any part or combination of parts of a donor body, including organs, tissues, and cells.

As used herein, "chimera" means a recipient comprising cells from the recipient and cells from at least one donor.

As used herein, "syngeneic" means of donor origin wherein the donor is genetically identical to the recipient.

As used herein, "allogeneic" means of donor origin wherein the donor is of the same species as the recipient.

As used herein, "xenogeneic" means of donor origin wherein the donor is of a different species than the recipient.

As used herein, "mixed chimeric immune system" means a recipient immune system comprising about 0.5% to 99% allogeneic or xenogeneic cells and the remaining percentage of syngeneic cells.

As used herein, "completely allogeneic cell chimeric immune system" means a recipient immune system created through the administration of both allogeneic and syngeneic cells and comprising virtually 100% allogeneic cells but in which some residual syngeneic cells providing for a limited number of immunological cell lineages may exist.

As used herein, "completely xenogeneic chimeric immune system" means a recipient immune system created through the administration of both syngeneic and xenogeneic cells and comprising virtually 100% xenogeneic cells but in which some residual syngeneic cells providing for a limited number of immunological cell lineages may exist.

4. BRIEF DESCRIPTION OF THE DRAWINGS

FIG. 1 Transmission electron micrograph of purified FC.

5. DETAILED DESCRIPTION OF THE INVENTION

The present invention relates to mammalian hematopoietic FC, to methods of isolating and characterizing the FC, and to methods of using the same.

While initial negative selection studies led to the view that the hematopoietic facilitatory cell was $CD8^-$, subsequent studies described herein have resulted in the conclusion that the proper phenotype of FC include $CD8^+$. Experimental data contained herein leading to the early conclusion regarding $CD8^-$ are retained for informational content only (see Section 6, infra), as the facilitatory cell is now conclusively demonstrated to be $CD8^+$ by positive selection studies (see Section 7, infra). These seemingly contradictory results are probably due to incomplete elimination of cells which express CD8 at low density when treated with antibody plus complement in the negative selection method used in Section 6. In the flow cytometry studies employing anti-CD8 monoclonal antibody for positive selection, a small population of $CD8^+$ cells is identified, which exhibit facilitatory activities. Similar observation occurred for CD3 as a FC marker. Although removal of $CD3^+$ cells by negative selection approaches did not eliminate the FC, FC is shown to be $CD3^+$ by cell sorting and add-back experiments. The cell sorter is much more sensitive and precise to identify antigens in small density on cell surfaces.

In addition, it was also originally thought that the facilitatory cell population was Class II bright. This determination was made by inference based on anti-Class II antibody depletion studies. In subsequent positive selection plus add back experiments, it was demonstrated that the facilitatory cell was not in the Class II bright fraction, but instead expressed Class II molecules in the range of dim to intermediate staining levels. This was determined by antibody staining and flow cytometry in which three levels of staining intensity were distinguished by comparing with other cell types as controls. For example, Class $II^-$ cells were used as background and brightly staining Class $II^+$ antigen presenting cells such as B cells and dendritic cells were considered Class $II^{bright}$. Furthermore, simultaneous morphological studies described herein (Section 7, infra) with electron microscopy have identified the Class II bright fraction as lymphocytes. Thus, the FC are Class II positive but not Class II bright, as compared with B cells.

The invention is discussed in more detail in the subsections below, solely for purposes of description and not by way of limitation. For clarity of discussion, the specific procedures and methods described herein are exemplified using a murine model; they are merely illustrative for the practice of the invention. Analogous procedures and techniques are equally applicable to all mammalian species, including human subjects, in terms of using the FC used as donor and a human recipient receiving such cells in transplantation. Therefore, human FC having a similar phenotype and function may be used under the conditions described herein. Further, non-human animal FC may also be used to enhance engraftment of xenogeneic cells in human patients.

5.1. Characterization of Facilitatory Cells

The model for mixed chimerism, in which syngeneic (host) plus allogeneic or xenogeneic (donor) bone marrow are co-administered following lethal total body irradiation has allowed identification of the facilitatory cell. Treatment of the donor bone marrow inoculum to remove, or to select and then add-back various cellular subsets to bone marrow depleted of T-cells using RAMB or THY1 or monoclonal antibodies to various CD markers, has shown a dramatic influence on the engraftment of allogeneic bone marrow and the overall level of mixed allogeneic chimerism. If TCD of both the syngeneic and allogeneic components of the mixed bone marrow inoculum is carried out, mixed multilineage lymphohematopoietic chimerism occurs. There is evidence that both the syngeneic and allogeneic stem cells co-engraft, since a mixture of host and donor red blood cell, platelets, T-cells, B-cells, cells of myeloid lineage, and NK cells are detectable. Each lineage is independently regulated since the level of lymphoid chimerism is not identical to that for other lineages. However, the percentage of allogeneic chimerism for each lineage remains remarkably stable, with little fluctuation, for the life of the recipient, up to about 12 months.

When the allogeneic component of the bone marrow inoculum is depleted of cells expressing THY1, mixed chimerism is observed. In striking contrast, if untreated allogeneic bone marrow is administered, facilitation of allogeneic stem cell engraftment results, and 100% allogeneic chimerism occurs. This effect is very potent since dose titration studies show that the graft-facilitating effect is reliably obtained when TCD allogeneic bone marrow cells failed to engraft; resulting in exclusively syngeneic repopulation. Similar facilitation of allogeneic stem cell engraftment occurs if CD4+, NK cells, mature monocytes and macrophages, or B-cells are removed. Thus, the mixed chimerism model provides an in vivo model for the identification and characterization of the cells capable of engraftment facilitating activities.

The studies described herein demonstrate that the facilitatory cell is not a stem cell since (1) treatment with anti-RAMB removes the facilitating effect for allogeneic bone marrow engraftment in rodents, in which engraftment more readily occurs than in humans, but mixed chimerism results (in contrast with 100% allogeneic engraftment), and (2) THY1.2 depletion of the allogeneic mouse bone marrow also removes the facilitating effect, but the balance of syngeneic:allogeneic engraftment in the form of mixed chimerism is slightly greater than after RAMB treatment. Although some batches of RAMB are well characterized to remove the bone marrow stem cell, this effect is excluded in syngeneic (A→A) reconstitution studies prior to their use in other experiments, since removal of all stem cells from the bone marrow would result in death from failure of engraftment.

One possible explanation is that THY1.2 depletion, or RAMB depletion of bone marrow, leads to selective depletion of bone marrow progenitor cells. However, when graded numbers of TCD versus untreated syngeneic bone marrow cells are administered to lethally irradiated mice, survival curves are similar for both groups, indicating that both bone marrow preparations have similar reconstituting ability. In this case of syngeneic reconstitution, the "facilitating cell" which is relatively radioresistant, exists endogenously in the recipient mouse. Therefore, stem cell depletion following antibody treatment is unlikely to account for the reduced levels of chimerism seen in recipients of TCD versus untreated allogeneic bone marrow.

Further, the hematopoietic stem cells and the FC described herein have a different profile of cell surface marker expression. U.S. Pat. No. 5,061,620 purports to characterize bone marrow stem cells as being for the most part $CD34^+$, $CD3^-$, $CD7^-$, $CD8^-$, $CD10^-$, $CD14^-$, $CD15^-$, $CD19^-$, $CD20^-$, $CD33^-$, and $THY1^+$. Moreover, the true hematopoietic stem cell is believed to be Class $II^-$. The THY1 marker is present on mouse T-cells, NK cells, and some myeloid cells, while it is absent on mature T-cells in the rat and human. When the purified cells are transplanted into a genetically identical recipient, engraftment usually occurs. However, these highly purified cells do not engraft in genetically different allogeneic or xenogeneic recipients.

The studies described herein show that the pluripotent bone marrow stem cell is not Class II positive. Using two different approaches to remove Class II positive cells (flow cytometry with negative selection and by antibody plus complement treatment), the facilitating effect for allogeneic stem cell engraftment is removed, eliminating complete allogeneic engraftment leading to multilineage mixed chimerism. If the stem cell had been removed by these depletions, exclusively syngeneic repopulation would have occurred.

Although the bone marrow stem cell fraction described by U.S. Pat. No. 5,061,620 is also THY1 positive, the distinction between THY1 low positivity versus THY1 bright positivity is critical. Reference to this difference allowed an approach to enrich for the stem cell, since the level of THY1 antigen expression on stem cells was not appreciated by those skilled in the art until recently (Spangrude et al., 1988, *Science* 241:58) and was a critical factor in allowing separation of committed (more mature) stem cell progeny versus less differentiated cells. (See also Spangrude, 1989, *Immunology Today* 10:344). Additionally, a recent report shows that there is no expression of THY1 on stem cells in mice possessing the THY1.2 allele (Spangrude and Brooks, 1992, *Blood* 80:1957).

In striking contrast, purification of the facilitating cell relies upon enrichment for the Class II positive cell fraction. Moreover, these cells alone in the absence of stem cells do not reconstitute a lethally irradiated syngeneic (A→A) recipient, while only 50–100 syngeneic stem cells are sufficient for rescue from lethal irradiation in the mouse.

Detailed analyses of human bone marrow, following the same procedures reveal a population of Class $II^+$cells with similar forward and side scatter on flow cytometry which are $CD34^-$. It is believed that this represents the human facilitating cell population. Like the corresponding cells in rodents, the human cells are negative for B-cell(CD19, CD20), monocyte,/macrophage (CD14), and T-cell (CD4, αβ-TCR, CD3) markers. A monoclonal antibody equivalent to anti-CD34 does not exist for rodent stem cells so comparison with CD34 staining versus the putative facilitating cell population cannot be performed.

As the FC are a novel cell population it is possible that the FC express other markers which have not yet been identified. If so, previous failure in identifying these unique molecules might be due to their decreased or lack of expression in other hematopoietic cell types. Therefore, the FC may be used to generate antibodies against their cell surface antigens in order to identify and characterize such unknown markers. Such antibodies may be useful in the further characterization and purification of these cells.

Also within the scope of the invention is the production of polyclonal and monoclonal antibodies which recognize novel antigenic markers expressed by FC, especially of human and rodent origin. Various procedures known in the art may be used for the production of antibodies to these cells after they have been isolated. For the production of antibodies, various host animals can be immunized by injection with viable, purified or partially purified FC, fixed cells or membrane preparations, including, but: not limited to, those of rabbits, hamsters, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Monoclonal antibodies to novel antigens on FC may be prepared by using any technique which provides for the production of antibody molecules by continuous cell lines in culture. These include, but are not limited to, the hybridoma technique originally described by Kohler and Milstein (1975, *Nature* 256, 495–497), the more recent human B-cell hybridoma technique (Kosbor et al., 1983, *Immunology Today* 4:72; Cote et al., 1983, *Proc. Natl. Acad. Sci. USA* 80:2026–2030) and the EBV-hybridoma technique (cole et al., 1985, *Monoclonal Antibodies and Cancer Therapy Alan R. Liss. Inc.*, pp. 77–96).

Syngeneic, allogeneic, and xenogeneic hosts may be immunized with FC which can be prepared in viable form, or in fixed form, or as extracted membrane fragments. Monoclonal antibodies can be screened differentially by selective binding to FC, but not to mature macrophages, granulocyte, dendritic cells, T, B cells and stem cells.

Antibody fragments which contain the binding site of the molecule may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments.

The activity of FC in enhancing donor cell engraftment also suggests a mechanism involving cell-cell interaction and/or cytokine production. In order to identify potential new cytokines produced by the FC, long-term FC cultures may be established or continuous cell lines may be generated by transforming the FC to tumor cells using a virus or a chemical. Culture supernatants may be directly analyzed by applying them to various cell types used as indicators which are known to respond to specific cytokines in bioassays. Cells may be metabolically labelled and their supernatants subjected to biochemical analysis. Having identified a major protein by SDS-PAGE and/or by biologic activity, the protein may be purified by SDS-preparative gels, ion exchange chromatography, and isoelectric focusing gels. Purity of the proteins can be verified by SDS-PAGE, quantified by protein assays, their activities confirmed in bioassays, and used as immunogens for the production of polyclonal and monoclonal antibodies.

The purified proteins can be further tested in bioassays to stimulate and/or inhibit proliferation and/or differentiation of a variety of indicator cell lines of diverse tissue types. Radiolabelled proteins may also be used to identify their cell surface receptors by methods such as affinity labelling. Specific antibodies to the cytokines may be used to identify and quantify membrane forms and secreted forms of the cytokines, to study their biosynthetic pathways, to affinity purify the proteins and to immunoscreen expression libraries for the molecular cloning of the coding sequences.

5.2. Isolation of Facilitatory Cells

The present invention provides for methods of enriching and/or purifying FC from bone marrow or other physiological sources of hematopoietic cells. The activity of the FC allows for their use in relatively small numbers when enriched from their original source, and absolute purity is not necessary. The FC may be isolated from any tissue where they reside, using a variety of separation procedures. Section 7, infra presents variants of such methods as illustration for isolating FC from the bone marrow. In accordance with this aspect of the invention, FC may be isolated by separations based on the presence or absence of specific markers.

Although bone marrow is preferred, other physiologic sources of hematopoietic cells may be utilized, for example, the spleen, thymus, blood, embryonic yolk sac, or fetal liver. Bone marrow is preferably removed from the femora or tibia, but may also be removed from the spine or other bone cavity. Bone marrow may be removed from bone cavity by various methods well known to those skilled in the art, including flushing the bone with a mixture of physiological media, balanced salt solution, physiological buffer, and other naturally occurring factors. Typically, the bone marrow is filtered, centrifuged and resuspended.

Once a source of hematopoietic cells is obtained, hematopoietic FC may be obtained by various methods which utilize specific antibodies which preferably bind specific markers to select those cells possessing or lacking various markers. These techniques may include, for example, flow cytometry using a fluorescence activated cell sorter (FACS) and specific fluorochromes, biotin-avidin or biotin-streptavidin separations using biotin conjugated to cell surface marker-specific antibodies and avidin or streptavidin bound to a solid support such as affinity column matrix or plastic surfaces, magnetic separations using antibody-coated magnetic beads, destructive separations such as antibody and complement or antibody bound to cytotoxins or radioactive isotopes.

Separation via antibodies for specific markers may be by negative or positive selection procedures. In negative separation, antibodies are used which are specific for markers present on undesired cells. Cells bound by an antibody may be removed or lysed and the remaining desired mixture retained. In positive separation, antibodies specific for markers present on the desired cells are used. Cells bound by the antibody are separated and retained. It will be understood that positive and negative separations may be used substantially simultaneously or in a sequential manner. It will also be understood that the present invention encompasses any separation technique which can isolate cells based on the characteristic phenotype of the FC as disclosed herein.

Until now, the most common technique for antibody based separation has been the use of flow cytometry such as by a FACS. Typically, separation by flow cytometry is performed as follows. The suspended mixture of hematopoietic cells are centrifuged and resuspended in media. Antibodies which are conjugated to fluorochrome are added to allow the binding of the antibodies to specific cell surface markers. The cell mixture is then washed by one or more centrifugation and resuspension steps. The mixture is run through a FACS which separates the cells based on different fluorescence characteristics. FACS systems are available in varying levels of performance and ability, including multi-color analysis. The facilitating cell can be identified by a characteristic profile of forward and side scatter which is influenced by size and granularity, as well as by positive and/or negative expression of certain cell surface markers.

Other separation techniques besides flow cytometry may provide for faster separations. One such method is biotin-avidin based separation by affinity chromatography. Typically, such a technique is performed by incubating the washed bone marrow with biotin-coupled antibodies to specific markers followed by passage through an avidin column. Biotin-antibody-cell complexes bind to the column via the biotin-avidin interaction, while other cells pass through the column. Finally, the column-bound cells may be released by perturbation or other methods. The specificity of the biotin-avidin system is well suited for rapid positive separation.

Flow cytometry and biotin-avidin techniques provide highly specific means of cell separation. If desired, a separation may be initiated by less specific techniques which, however, can remove a large proportion of "non-facilitating" cells from the hematopoietic cell source. For example, magnetic bead separations may be used to initially remove "non-facilitating" differentiated hematopoietic cell populations, including T-cells, B-cells, natural killer (NK) cells, and macrophages (MAC), as well as minor cell populations including megakaryocytes, mast cells, eosinophils, and basophils. Desirably, at least about 70% and usually at least about 80% of the total hematopoietic cells present can be removed.

A preferred initial separation technique is density-gradient separation. Here, the bone marrow or other hematopoietic cell mixture preparation is centrifuged and the supernatant removed. The cells are resuspended in, for example, RPMI 1640 medium (Gibco) with 10% FCS and placed in a density gradient prepared with, for example, Ficoll or Percoll or Eurocollins media. The separation may then be performed by centrifugation or may be performed automatically with, for example, a Cobel & Cell Separator '2991 (Cobev, Lakewood, Colo.). Additional separation procedures may be desirable depending on the source of the hematopoietic cell mixture and on its content. For example, if blood is used as a source of hematopoietic cells, it may be desirable to lyse red blood cells prior to the separation of any fraction. Furthermore, elutriation may also be used alone or in combination with all of other purification procedures described herein (Noga et al., 1990, *Prog. Clin. Biol. Res.* 333:345; Noga et al., 1992, *Prog. Clin. Biol. Res.* 377:411).

The FC are generally characterized by being $\alpha\beta$-TCR$^-$, $\gamma\delta$-TCR$^-$, CD4$^-$, CD5$^-$, CD16$^-$, CD19$^-$, CD20$^-$, CD56$^-$, mature myeloid lineage⁻ (CD14⁻), Class II⁺, CD45⁺, CD45R⁺, THY1⁺, CD8⁺, and CD3⁺. A high concentration of FC may be obtained by positive separation of a mixture of hematopoietic cells into a facilitatory cell containing fraction which is Class II⁺ and THY1⁺. The Class II⁺ fraction may be further separated based on staining intensity and the Class II bright population eliminated.

A high concentration of FC may be obtained by positive separation of a mixture of hematopoietic cells into a facilitatory cell containing fraction which is Class II⁺ and CD45R⁺. A higher concentration of FC may be obtained by separating a mixture of hematopoietic cells into a fraction which is Class II⁺, CD45R⁺, and THY1⁺.

As stated hereinabove, the specific markers used to separate cells will depend on the source of the hematopoietic cell mixture. About 1% to 8% of bone marrow is Class II positive. At least 80% of bone marrow cells are removed by negative selection using those markers described herein which the facilitatory cell does not possess. If the source of hematopoietic cells is bone marrow, a high concentration of FC may be obtained by a large number of different negative selection sequences. A still higher concentration of FC may be obtained by positive separation of the bone marrow into a fraction which is Class II⁺. An even higher concentration can be obtained by further separating this Class II⁺ fraction into a fraction which is CD19⁻.

Although separations based on specific markers are disclosed, it will be understood that the present invention encompasses any separation based on the characterization of the FC disclosed herein which will result in a cellular composition comprising a high concentration of FC, whether that separation is a negative separation, a positive separation, or a combination of negative and positive separations, and whether that separation uses cell sorting or some other technique, such as, for example, antibody plus complement treatment, column separations, panning, biotin-avidin technology, density gradient centrifugation, or other techniques known to those skilled in the art. It will be appreciated that the present invention encompasses these separations used on any mammal including, but not limited to humans, primates, baboons, rats, mice, and other rodents.

The source of the hematopoietic cell mixture will determine the amount of mixture required to obtain a large enough sample of FC. The source of the hematopoietic cell mixture will also determine the time necessary to obtain a large enough sample. For example, the concentration of FC in blood is relatively minute and separation of a fraction of purified FC from blood will require a large amount of blood and a relatively long time to separate compared to, for example, using bone marrow as a source of the hematopoietic cell mixture.

FC make up between about 0.5% and 8% of the cells found in physiological hematopoietic cell sources. Separations such as those disclosed herein can yield cellular compositions comprising a substantially greater number of FC than found naturally in physiological hematopoietic cell sources. For example, cellular compositions in which at least about 30% of the cells are hematopoietic FC characterized as stated hereinbefore are provided, and cellular compositions in which at least about 95% of the cells are hematopoietic FC characterized as stated hereinbefore are also provided. Proper selection of markers can provide a substantially pure population of FC for in vivo use.

5.3. Uses of Facilitatory Cells

The ability of FC to enhance engraftment of bone marrow donor cells in an allogeneic or xenogeneic recipient indicates that they may be useful in facilitating various therapy protocols involving transplantation procedures. Formulation of a cellular composition comprising a high concentration of hematopoietic FC provides a solution to the alternative problems of GVHD and failure of engraftment. Alternatively, donor marrow depleted of T cells, with the retention of FC, may also be used for transplantation. The present invention provides for the use of FC in establishing a mixed allogeneic or mixed xenogeneic chimeric immune system, completely allogeneic or completely xenogeneic chimeric hematopoietic system. Generally, the methods of the present invention relate to the administration of cellular compositions comprising purified donor FC to a recipient along with MHC-specific donor stem cells and any additional donor bone marrow components desired, but T-cells are preferably depleted. If mixed or completely allogeneic or xenogeneic chimerism is desired, syngeneic or autologous cellular compositions which comprise FC and stem cells are administered along with the donor cell compositions. However, it is not required that FC be used with other donor cells that are autologous or syngeneic to the host. Allogeneic or xenogeneic FC may be used with MHC-matched bone marrow cells to reconstitute a recipient, without co-administration of autologous or syngeneic donor cells.

Studies designed to demonstrate that the FC of the present invention are not T cells yet are capable of enhancing engraftment have been performed in both allogeneic and xenogeneic settings (See Examples 6–10, infra). It is noteworthy that allogeneic bone marrow transplantation appears to be the easiest to perform in certain animal models such as between mice of different strains. Therefore, mouse donor bone marrow cells treated with RAMB or anti-Thy antibodies are still usually able to cause some level of chimerism in an allogeneic host, albeit at a lower level of engraftment than if the reconstitution is carried out with the retention of FC. However, xenogeneic bone marrow transplantation of rat donor cells into mice is generally more difficult to achieve with donor cells after TCD, as manifested by death of the recipients as a result of failure of engraftment. The findings in xenogeneic bone marrow transplantation much more closely resemble the result observed in human allogeneic bone marrow transplantation in that TCD of allogeneic donor bone marrow cells leads to high mortality due to failure of engraftment. Therefore, the ability of the FC to enhance xenoengraftment and xenogeneic chimerism in animal models indicates that these cells may be used successfully in human allogeneic bone marrow transplantation. For unknown reasons, allogeneic bone marrow transplantation in dogs and pigs appears to be the most difficult to achieve.

The FC are capable of facilitating engraftment of stem cells and other bone marrow components which are MHC-specific to the FC. It is possible that particular species or certain strains of particular species possess FC which are also capable of facilitating engraftment of stem cells and other bone marrow components which are not MHC-specific, as traditionally understood, to the facilitatory cell. For convenience, these FC will be referred to as universal FC. Cellular compositions comprising such cells are also encompassed by the present invention. Furthermore, it is possible that FC and stem cells need not be matched at their MHC entirely. There are subregions within both Class I and Class II genes of the MHC. Thus, a matching at only one of these regions may be sufficient for the FC to enhance stem cell engraftment. Studies directed towards defining such important MHC subregions are best carried out in mice, utilizing various commercially available MHC recombinant inbred mouse stains.

Generally, purified or partially purified FC facilitate engraftment of stem cells which are MHC-specific to the FC so as to provide superior survival of the chimeric immune system. The stem cells and FC preferably come from a common donor or genetically identical donors. However, if the donor is of a species or a strain of a species which possesses a universal facilitatory cell, the stem cells need not be MHC-specific to the facilitatory cell. By purifying the FC separately, either by positive selection, negative selection, or a combination of positive and negative selection, and then administering them to the recipient along with MHC-specific stem cells and any desired additional donor bone marrow components, GVHD causing T-cells may be removed without fear of failure of engraftment. As a result, mixed or completely or fully allogeneic or xenogeneic repopulation can be achieved.

One embodiment of a method of establishing an allogeneic or xenogeneic chimeric immune system comprises substantially destroying the immune system of the recipient. This may be accomplished by techniques well known to those skilled in the art. These techniques result in the substantially full ablation of the bone marrow-stem cells of the recipient. However, there may be some resistant recipient stem cells which survive and continue to produce specific immune cells. These techniques include, for example, lethally irradiating the recipient with selected levels of radiation, administering specific toxins to the recipient, administering specific monoclonal antibodies attached to toxins or radioactive isotopes, or combinations of these techniques.

Bone marrow is harvested from the long bones of the donor. For allogeneic chimerism, donor and recipient are the same species; for xenogeneic chimerism, donor and recipient are different species. A cellular composition comprising a high concentration of FC is separated from other donor bone marrow cells by the methods disclosed in Section 5.2, supra. A separate cellular composition comprising a high concentration of hematopoietic progenitor stem cells is separated from the remaining donor bone marrow. Separation of a cellular composition comprising a high concentration of stem cells may be accomplished by techniques such as those used to purify FC, but based on different markers, most notably CD34 stem cell separation techniques include the methods disclosed in U.S. Pat. No. 5,061,620 and the separate LC Laboratory Cell Separation System, CD34 kit manufactured by CellPro, Incorporated of Bothell, Wash. The purified donor facilitatory cell composition and purified donor stem cell composition are then preferably mixed in any ratio. However, it is not necessary to mix these cellular compositions.

If the facilitatory cell is purified by negative selection using any or all of the markers disclosed herein not to be expressed on the facilitatory cell, then the resulting cellular composition will contain stem cells as well as FC and other immature progenitor cells. Antibodies directed to T cell specific markers such as anti-CD3 and anti-TCR$\alpha\beta$ may be used to specifically eliminate GVHD-producing cells, while retaining hematopoietic facilitatory and stem cells without a need for substantial purification. In such a case, this one cellular composition may take the place of the two cellular compositions referred to hereinabove which comprise both purified FC and purified stem cells.

The purified donor FC and purified donor stem cells are then administered to the recipient. If these cellular compositions are separate compositions, they are preferably administered simultaneously, but may be administered separately within a relatively close period of time. The mode of administration is preferably but not limited to intravenous injection.

Once administered, it is believed that the cells home to various hematopoietic cell sites in the recipient's body, including bone cavity, spleen, fetal or adult liver, and thymus. The cells become seeded at the proper sites. The cells engraft and begin establishing a chimeric immune system. Since non-universal FC must be MHC-specific, as traditionally understood, with the stem cells whose engraftment they facilitate, it is possible that both the stem cells and FC bond together to seed the appropriate site for engraftment.

The level of alloengraftment or xenoengraftment is a titratable effect which depends upon the relative numbers of syngeneic cells and allogeneic or xenogeneic cells and upon the type and degree of conditioning of the recipient. Completely allogeneic or xenogeneic chimerism should occur if the FC of the syngeneic component have been depleted by TCD procedures or other techniques, provided that a threshold number of allogeneic or xenogeneic FC are administered. A substantially equal level of syngeneic and allogeneic or xenogeneic engraftment is sought. The amount of the various cells which should be administered is calculated for a specific species of recipient. For example, in rats, the T-cell depleted bone marrow component administered is typically between about $1 \times 10^7$ cells and $5 \times 10^7$ cells per recipient. In mice, the T-cell depleted bone marrow component administered is typically between about $1 \times 10^6$ cells and $5 \times 10^6$ cells per recipient. In humans, the T-cell depleted bone marrow component administered is typically between about $1 \times 10^8$ cells and $3 \times 10^8$ cells per kilogram body weight of recipient. For cross-species engraftment, larger numbers of cells may be required.

In mice, the number of purified FC administered is preferably between about $1 \times 10^4$ and $4 \times 10^5$ FC per recipient. In rats, the number of purified FC administered is preferably between about $1 \times 10^6$ and $30 \times 10^6$ FC per recipient. In humans, the number of purified FC administered is preferably between about $1 \times 10^6$ and $10 \times 10^6$ FC per kilogram recipient.

In mice, the number of stem cells administered is preferably between about 100 and 300 stem cells per recipient. In rats, the number of stem cells administered is preferably between about 600 and 1200 stem cells per recipient. In humans, the number of stem cells administered is preferably between about $1 \times 10^5$ and $1 \times 10^6$ stem cells per recipient. The amount of the specific cells used will depend on many factors, including the condition of the recipient's health. In addition, co-administration of cells with various cytokines may further promote engraftment.

In addition to total body irradiation, a recipient may be conditioned by immunosuppression and cytoreduction by the same techniques as are employed in substantially destroying a recipient's immune system, including, for example, irradiation, toxins, antibodies bound to toxins or radioactive isotopes, or some combination of these techniques. However, the level or amount of agents used is substantially smaller when immunosuppressing and cytoreducing than when substantially destroying the immune system. For example, substantially destroying a recipient's remaining immune system often involves lethally irradiating the recipient with 950 rads (R) of total body irradiation (TBI). This level of radiation is fairly constant no matter the species of the recipient. Consistent xenogeneic (rat→mouse) chimerism has been achieved with 750 R TBI and consistent allogeneic (mouse) chimerism with 600R TBI. Chimerism was established by PBL typing and tolerance confirmed by mixed lymphocyte reactions (MLR) and cytotoxic lymphocyte (CTL) response.

As stated hereinbefore, the above disclosed methods may be used for establishing both allogeneic chimerism and xenogeneic chimerism. Xenogeneic chimerism may be established when the donor and recipient as recited above are different species. xenogeneic chimerism between rats and mice, between hamsters and mice, and between chimpanzees and baboons has been established. Xenogeneic chimerism between humans and other primates is also possible. Xenogeneic chimerism between humans and other mammals is equally viable.

It will be appreciated that, though the methods disclosed above involve one recipient and one donor, the present invention encompasses methods such as those disclosed in which stem cells and purified FC from two donors are engrafted in a single recipient.

It will be appreciated that the present invention also provides methods of reestablishing a recipient's hematopoietic system by substantially destroying the recipient's immune system or immunosuppressing and cytoreducing the recipient's immune system, and then administering to the recipient syngeneic or autologous cell compositions comprising syngeneic or autologous purified FC and stem cells which are MHC-identical to the FC.

The ability to establish successful allogeneic or xenogeneic chimerism allows for vastly improved survival of transplants. The present invention provides for methods of transplanting a donor physiological component, such as, for example, organs, tissue, or cells. Examples of successful transplants in and between rats and mice using these methods include, for example, islet cells, skin, hearts, livers, thyroid glands, parathyroid glands, adrenal cortex, adrenal medullas, and thymus glands. The recipient's chimeric immune system is completely tolerant of the donor organ, tissue, or cells, but competently rejects third party grafts. Also, bone marrow transplantation confers subsequent tolerance to organ, tissue, or cellular grafts which are genetically identical or closely matched to the bone marrow previously engrafted.

Transplanted donor organ, tissue, or cells competently perform their function in the recipient. For example, transplanted islet cells function competently, and thereby provide an effective treatment for diabetes. In addition, transplantation of bone marrow using methods of the present invention can eliminate the autoimmune diabetic trait before insulin-dependence develops. Successful solid organ transplants between humans and animals may be performed using methods of the present invention involving hematopoietic FC. For example, islet cells from other species may be transplanted into humans to treat diabetes in the human recipient after the disease is diagnosed or after the onset of insulin dependence. Major organs from animal donors such as, for example, pigs, cows or fish can solve the current problem of donor shortages. For example, 50% of patients who require a heart transplant die before a donor is available. It has been demonstrated that permanent acceptance of endocrine tissue engrafts (thyroid, parathyroid, adrenal cortex, adrenal medulla, islets) occurs in xenogeneic chimeras after bone marrow transplantation from a genetically identical donor. Hence, mixed xenogeneic chimerism or fully xenogeneic chimerism established by methods of the present invention can be employed to treat endocrine disorders as well as autoimmunity, such as, for example, diabetes.

The methods of the present invention involve transplanting the specific donor physiological component by methods known to those skilled in the art and, in conjunction with establishing a chimeric immune system in the recipient using the transplant donor as the donor of the purified donor facilitatory cell composition and donor stem cell composition. A mixed chimeric immune system is preferred. The method of establishing a mixed chimeric immune system may be performed before, during, or after the transplantation, but is preferably performed before the transplantation, especially since immunosuppression and cytoreduction or immunodestruction is necessary in the chimeric methods as disclosed herein. The methods disclosed allow for both allotransplantation and xenotransplantation. Because the methods disclosed herein provide for donor-specific immunotolerance, many procedures previously necessary to resist rejection of the donor organ, tissue, or cells are unnecessary. For example, live bone and cartilage may be transplanted by the herein disclosed method.

Cell farming technology can provide for a readily available supply of FC, stem cells and genetically matched physiological donor components. For example, bone marrow cells enriched for the facilitatory cell can be propagated in vitro in cultures and/or stored for future transplantation. Cellular material from the same donor can be similarly stored for future use as grafts.

Beyond transplantation, the ability to establish a successful allogeneic or xenogeneic chimeric hematopoietic system or to reestablish a syngeneic or autologous hematopoietic system can provide cures for various other diseases or disorders which are not currently treated by bone marrow transplantation because of the morbidity and mortality associated with GHVD. Autoimmune diseases involve attack of an organ or tissue by one's own immune system. In this disease, the immune system recognizes the organ or tissue as a foreign. However, when a chimeric immune system is established, the body relearns what is foreign and what is self. Establishing a chimeric immune system as disclosed can simply halt the autoimmune attack causing the condition. Also, autoimmune attack may be halted by reestablishing the victim's immune system after immunosuppression and cytoreduction or after immunodestruction with syngeneic or autologous cell compositions as described hereinbefore. Autoimmune diseases which may be treated by this method include, for example, type I diabetes, systemic lupus erythematosus, multiple sclerosis, rheumatoid arthritis, psoriasis, colitis, and even Alzheimers disease. The use of the FC plus stem cell can significantly expand the scope of diseases which can be treated using bone marrow transplantation.

Because a chimeric immune system includes hematopoietic cells from the donor immune system, deficiencies in the recipient immune system may be alleviated by a nondeficient donor immune system. Hemoglobinopathies such as sickle cell anemia, spherocytosis or thalassemia and metabolic disorders such as Hunters disease, Hurlers disease, and enzyme defects, all of which result from deficiencies in the hematopoietic system of the victim, may be cured by establishing a chimeric immune system in the victim using purified donor hematopoietic FC and donor stem cells from a normal donor. The chimeric immune system should preferably be at least 10% donor origin (allogeneic or xenogeneic).

The ability to establish successful xenogeneic chimerism can provide methods of treating or preventing pathogen-mediated disease states, including viral diseases in which species-specific resistance plays a role. For example, AIDS is caused by infection of the lymphohematopoietic system by a retrovirus (HIV). The virus infects primarily the $CD4^+$ T cells and antigen presenting cells produced by the bone marrow stem cells. Some animals, such as, for example, baboons, possess native immunity or resistance to AIDS. By establishing a xenogeneic immune system in a human recipient, with a baboon or other AIDS resistant and/or immune animal as donor, the hematopoietic system of the human recipient can acquire the AIDS resistance and/or immunity of the donor animal. Other pathogen-mediated disease states may be cured or prevented by such a method using animals immune or resistant to the particular pathogen which causes the disease. Some examples include hepatitis A, B, C, and non-A, B, C hepatitis. Since the facilitatory cell plays a major role in allowing engraftment of stem cells across a species disparity, this approach will rely upon the presence of the facilitatory cell in the bone marrow inoculum.

The removal of the facilitatory cell has been shown to substantially impair engraftment across species differences. However, while not the preferred approach, untreated xenogeneic bone marrow will engraft if sufficient cells are administered. Bone marrow derived cells could be used in this case to treat or prevent AIDS with or without enrichment for the facilitatory cell. Previous studies demonstrated that GVHD could occur across a species barrier. Therefore, the preferred approach would be to establish the xenogeneic chimeric immune system using cellular compositions comprising purified donor FC by methods disclosed herein or compositions depleted of T cells.

Furthermore, some animals, such as, for example, baboons and other non-human primates, possess native immunity or resistance to hepatitis. By transplanting a liver from a baboon or other hepatitis resistant animal into a victim of hepatitis using a method of the present invention, wherein a xenogeneic chimeric immune system is established in the victim using purified donor FC plus stem cells, the donor liver will not be at risk for hepatitis, and the recipient will be tolerant of the graft, thereby eliminating the requirement for nonspecific immunosuppressive agents. Unmodified bone marrow or purified stem cells may suffice as the liver may serve as a hematopoietic tissue and may contain FC that will promote the engraftment of stem cells from the same donor.

Establishing a mixed chimeric immune system has also been found to be protective against cancer. Sykes et al., 1990 Proc. Natl. Acad. Sci., U.S.A., 87: 5633–5637). Although the mechanism is not known, it may be due to multiplication of immune cell tumor specificity by the combination of donor and recipient immune system cells.

Usually, mixed chimerism is preferred. However, fully allogeneic or fully xenogeneic chimerism may be preferred in certain instances. For example, the present invention provides a method of treating leukemia or other malignancies of the lymphohematopoietic system comprising substantially destroying the victim's immune system and establishing a fully allogeneic chimeric immune system by the methods described herein. Since the victim's own immune system is cancerous, it is preferred to fully replace the syngeneic cells with allogeneic cells of a non-cancerous donor. In this case, autologous purified stem cells and FC may be used in order to totally eliminate all cancer cells in the donor preparation, especially if high dose chemotherapy or irradiation is used to ablate endogenous FC.

The present invention also provides a method of resisting physiological effects of aging. Current research indicates aging is related to hormonal changes, such as, for example, lower growth hormone. These changes can result in decreased physiological and/or physicochemical protection, such as, for example, protection against free radicals. Using methods of the present invention, transplantation of the pituitary, pituitary and hypothalamus, or other endocrine tissues can provide renewed hormone levels.

The present invention also provides methods of practicing gene therapy. It has recently been shown that sometimes even autologous cells which have been genetically modified may be rejected by a recipient. Utilizing methods of the present invention, a chimeric immune system can be established in a recipient using hematopoietic cells which have been genetically modified in the same way as genetic modification of other cells being transplanted therewith. This will render the recipient tolerant of the genetically modified cells, whether they be autologous, syngeneic, allogeneic or xenogeneic.

It will be appreciated that the present invention discloses cellular compositions comprising purified FC cellular compositions depleted of T cells with the retention of FC and stem cells, methods of purifying FC, methods of establishing fully, completely or mixed allogeneic or xenogeneic chimeric immune systems, methods of reestablishing a syngeneic immune system, and methods of utilizing compositions of FC to treat or prevent specific diseases, conditions or disorders. It will also be appreciated that the present invention discloses methods of treating or preventing certain pathogen-mediated diseases by administering xenogeneic cells which have not been purified for the facilitatory cell.

Whereas particular embodiments of the invention has been described hereinbefore, for purposes of illustration, it would be evident to those skilled in the art that numerous variations of the details may be made without departing from the invention as defined in the appended claims.

6. EXAMPLE

Removal of Facilitatory Cells Reduces Allogeneic Bone Marrow Engraftment 6.1. Materials and Methods
6.1.1. Preparation of Mixed Allogeneic Chimeras To prepare mixed chimeras, bone marrow from the long bones of syngeneic mice and allogeneic mice were harvested. The mice were euthanized with $CO_2$ narcosis, prepared with 70% alcohol, and the long hind bone (femora and tibia) removed. The marrow was flushed from the bones using medium 199 (Gibco Laboratories Life Technology, Inc., Grand Island, N.Y.) supplemented with 50 $\mu$l/ml of gentamicin using a 22-gauge needle. The medium mixture (MEM) was used to mechanically resuspend the bone marrow by gentle aspiration through an 18-gauge needle and the suspension filtered through sterile nylon mesh gauze. The cells were then pelleted at 1000 rpm for 10 minutes, resuspended in MEM, and counted. In standard allogeneic reconstitution, RAMB was used for T-cell depletion (1:40 or appropriate dilution at $10^8$ cells/ml at 4° C. for 30 minutes). Cells were then washed in MEM, spun at 1000 rpm for 10 minutes and resuspended in guinea pig complement at 37° C. for 30 minutes (Gibco Laboratories Life Technology, Inc., Grand Island, N.Y.). Cells were washed twice, counted and resuspended in MEM at the appropriate concentration to allow injection of 1 ml of total volume per animal. Within 4–6 hours after irradiation of recipient animals, the cells were injected via the lateral tail veins using a 27-gauge needle.

6.1.2. Animals

Six to eight week old male C57BL/10SnJ (B10), B10. BR/SgSn (B10. BR), BALB/c mice were purchased from the Jackson Laboratory (Bar Harbor, Me.). Four to eight week old male Fischer 344 (F344), ACI and Wistar Furth (WF) male rats were purchased from Harlan Sprague Dawley, Inc. (Indianapolis, Ind.). Animals were housed in a specific pathogen-free facility at the Biomedical Science Tower at the University of Pittsburgh.

6.1.3. Depletion of Cellular Subsets from Bone Marrow

When cellular subset depletions were performed, bone marrow was harvested in a similar fashion. Treatment was carried out using anti-CD4 (L3T4, IgG2b, ATCC or RL1/72, IgM), anti-CD8 (LYT2, IgM, ATCC), anti-Thy1.2 (20-20-5 IgM; ATCC), anti-Mac-1 (IgG2b; ATCC), or anti-Class II IA$^k$ (IgM; ATCC) plus rabbit complement (C') prepared from New Zealand white retired breeder rabbits and previously screened in the laboratory. The incubation was at 37° C. for 45 minutes for antibody treatment followed by washing and 37° C. for 30 minutes with C' treatment; and washed two times. The remaining cells were often depleted for a second round with antibody and complement before use.

Because anti-NK1.1 antibody did not fix C', depletion of NK cells was performed using negative selection by flow cytometry. Bone marrow was harvested in the usual sterile fashion and staining with monoclonal antibody anti-NK1.1 performed in Hanks buffered saline solution to which 2% FCS plus gentamicin were added. The cell fraction which did not stain with NK1.1 antibody was collected and used as a NK-negative cell population.

Rabbit-anti-mouse-brain (RAMB) was a polyclonal antiserum prepared by immunizing rabbits with homogenized mouse brain. RAMB has been frequently used as an agent for depleting T-cells over the past few decades.

6.1.4. Characterization of Chimeras by Flow Cytometry

Recipients were characterized for engraftment with syngeneic, xenogeneic, allogeneic, syngeneic and xenogeneic, or syngeneic and allogeneic donor lymphoid elements using flow cytometry to determine the percentage of peripheral blood leukocytes (PBL) bearing MHC Class I (H-2b or H-2k) and Class I[RtI] rat anti-F344 [RtIA]$^1$], WF [RtIA$^U$], or ACI [RtIA$^a$] surface markers. Briefly, peripheral blood was collected into heparinized plastic serum vials. After thorough mixing, the suspension was layered over 1.5 ml of room temperature lymphocyte separation medium (LSM) (Organon Technical, Kensington, Md.) and centrifuged at 20° C. at 1700 rpm for 30 minutes. The lymphocyte layer was aspirated from the saline-LSM interface and washed with medium. Red blood cells were ACK-lysed (ammonium chloride/potassium carbonate lysing buffer) and the remaining cells stained with appropriate monoclonal antibodies (mAbs) for 30 minutes at 40° C. and counterstained with sandwich when required.

Analyses of splenic and thymic lymphoid cells were performed using a fluorescence activated cell sorter (FACS) (FACS II Becton Dickinson and Company, Mountain View, Calif.). Monoclonal antibodies anti-WF and anti-F344-Biotin were of rat origin and were utilized for Class I staining of rat cells. Anti-H2$^b$ mAb (28-8-6S) (IgG2a; HB31; American Type Culture Collection, Rockville, Md.) was utilized for class I staining. Anti-CD4-PE mouse, anti-THY1.2 PE, anti-CD8-FITC mouse (Becton Dickinson and Company), anti-TCR-αβ-FITC, anti-TCR-γδ, anti-B220 (anti-B-cell) and anti-Class II (IA$^k$ or IE$^k$) (Pharmangen, San Diego, Calif.) were utilized for cellular subset staining.

Data were displayed as cell frequency histograms in which log fluorescence intensity was displayed on the horizontal axis and relative cell number on the vertical axis. The percentage of cells considered positive after staining with the relevant mAb was calculated using a cut-off for positivity determined from the control fluorescence profiles of negative and positive control populations (B10 mouse and F344 rat). In addition, the relative size and granularity of cells were determined by flow cytometry using forward and side scatter. Lymphocytes and other cells with smaller size and lower granularity resided in one characteristic area, while larger and more granular cells such as macrophages and granulocyte resided in another.

6.2. Results

The experiments described in the following sections utilized a mixed chimeric model in which recipient animals were lethally-irradiated and transplanted with varying doses and subsets of allogeneic donor cells with or without co-administration of syngeneic cells. The percentage of allogeneic or xenogeneic chimerism, i.e., the level of mixed chimerism was used as a read-out of the efficiency of donor cell engraftment.

It is noteworthy that engraftment of allogeneic bone marrow between different strains of mice generally occurs with a relatively high frequency, i.e., TCD does not completely abrogate engraftment. However, xenogeneic engraftment is much more difficult to achieve, i.e., TCD of xenogeneic donor cells usually causes death of the recipient due to failure of engraftment. In fact, findings in xenogeneic engraftment performed in animal models much more closely resemble human allogeneic bone marrow transplantation results in that TCD of human allogeneic bone marrow cells usually leads to a high incidence of mortality. Thus, data presented in this section, in Examples 7 and 8, infra, in which allogeneic bone marrow cells were transplanted were primarily used to demonstrate the activity of the FC by measuring an increase in chimerism over a lower level of chimerism achieved by TCD donor cells. However, Example 9, infra presents results from xenogeneic transplants where engraftment was assessed in relation to death of recipients receiving TCD xenogeneic donor cells. Reconstitution of lethally irradiated recipients with TCD syngeneic (host-type) plus TCD allogeneic (donor-type) bone marrow (A+B→A) resulted in mixed multilineage lymphohematopoietic chimerism (Table 1; Group A). When only the syngeneic component of the bone marrow inoculum was TCD with RAMB, completely allogeneic engraftment resulted (Table 1; Group B). Hence, the syngeneic bone marrow stem cell was not eliminated by TCD, but the cell which facilitated its engraftment was.

TABLE 1

Effect of Depletion Of T-Cells Or MAC-1 Cells From The Allogeneic Component of The Mixed Bone Marrow Inoculum On Level of Allogeneic Chimerism●: Flow Cytometric Typing

| Group | Animal No. | Treatment of B10.BR Marrow | % Allogeneic Chimerism$^\Psi$ (H-2$^k$) |
|---|---|---|---|
| A | 11 | RAMB | 3.2 |
| | 12 | RAMB | 14.6 |
| | 13 | RAMB | 22.6 |
| | 14 | RAMB | 8.2 |
| B | 15 | NONE | 100* |
| | 16 | NONE | 100* |
| | 17 | NONE | 100* |
| | 18 | NONE | 100* |
| C | 19 | ANTI-CD8 | 100* |
| | 20 | ANTI-CD8 | 100* |
| | 21 | ANTI-CD8 | 100* |

TABLE 1-continued

Effect of Depletion Of T-Cells Or MAC-1 Cells From The Allogeneic Component of The Mixed Bone Marrow Inoculum On Level of Allogeneic Chimerism●:
Flow Cytometric Typing

| Group | Animal No. | Treatment of B10.BR Marrow | % Allogeneic Chimerism$^\Psi$ (H-2$^k$) |
|---|---|---|---|
| | 22 | ANTI-CD8 | 100* |
| D | 23 | ANTI-CD4 | 100* |
| | 24 | ANTI-CD4 | 100* |
| | 25 | ANTI-CD4 | 100* |
| | 26 | ANTI-CD4 | 100* |
| E | 27 | ANTI-CD4 + CD8 | 100* |
| | 28 | ANTI-CD4 + CD8 | 100* |
| | 29 | ANTI-CD4 + CD8 | 100* |
| | 30 | ANTI-CD4 + CD8 | 100* |
| | 31 | ANTI-CD4 + CD8 | 100* |
| | 32 | ANTI-CD4 + CD8 | 100* |
| | 33 | ANTI-CD4 + CD8 | 100* |
| F | 34 | ANTI-MAC 1 | 100* |
| | 35 | ANTI-MAC 1 | 100* |
| | 36 | ANTI-MAC 1 | 100* |
| | 37 | ANTI-MAC 1 | 100* |

$5 \times 10^6$ RAMB-treated B10 cells + $15 \times 10^6$ B10.BR cells → B10 host.
●This is one of 10 experimental groups prepared. All syngeneic bone marrow was RAMB-treated.
$^\Psi$Animals were PBL typed for chimerism at 6 weeks after reconstitution.
*No peak by flow cytometry. Numbers have been normalized to 100%.

TCD was almost certainly not a stem cell depletion effect since in syngeneic reconstitution studies, titration of number of cells to achieve engraftment showed similar survival curves whether untreated or TCD bone marrow was administered. Similar findings were obtained when RAMB treated marrow was administered or when anti-THY-1 monoclonal antibody plus C' treatment was utilized. In further studies using the mixed allogeneic chimera model, it was demonstrated that removal of CD4$^+$, CD8$^+$, CD4$^+$plus CD8$^+$, and MAC-1$^+$ cells using monoclonal antibodies plus C' did not eliminate allogeneic engraftment, i.e., 100% allogeneic chimerism resulted (Table 1; Groups C through F). This finding is particularly important clinically because cells expressing these markers appear to produce GVHD in humans, mice, and rats. CD4$^+$ cells, CD8$^+$ cells, B cells and to a lesser extent NK cells have been implicated in lethal and non-lethal GVHD. Removal of these subsets, therefore, would eliminate GVHD but not the facilitating cell.

The adequacy of depletion of the mixed allogeneic chimera models of Table 1 was confirmed by flow cytometry using either a non-cross-reactive monoclonal antibody or a saturation sandwich antibody technique (if a non-blocking second antibody to the same antigen was not available). Recipient animals were typed for levels of allogeneic and syngeneic chimerism using anti-Class I (H-2$^k$ and H-2$^b$) monoclonal antibodies and PBL at 6 weeks after reconstitution. Some animals were re-typed at 2, 4 and 6 months to follow kinetics of the chimerism.

Treatment of the allogeneic bone marrow inocula with anti-THY1.2 plus C' to remove THY1.2$^+$ cells resulted in a reduction of the facilitating effect, represented by mixed instead of completely allogeneic engraftment. The effect with anti-THY1.2 was not as dramatic as that with RAMB might be a result of the inability of anti-THY1.2 to completely eliminate all Thy1.2$^+$ cells. This treatment did not remove the allogeneic stem cell, since some allogeneic engraftment was observed; thus, it must have eliminated the facilitating effect which occurred when untreated marrow was administered (Table 2). Complement controls were performed for each experiment and the results were similar to those for untreated bone marrow.

TABLE 2

Effect of T-Cell Depletion From The Allogeneic Component Of Mixed Bone Marrow Inoculum On Level Of Allogeneic Chimerism

| Chimera Number | Treatment of Allogeneic Donor (B10.BR Marrow) | % Allogeneic (H-2$^k$) Chimerism$^\Psi$ |
|---|---|---|
| 1 | RAMB | 38.3 |
| 2 | RAMB | 40.3 |
| 3 | RAMB | 2.4 |
| 4 | RAMB | 1.7 |
| 5 | THY1.2 | 82.8 |
| 6 | THY1.2 | 79.4 |
| 7 | THY1.2 | 82.4 |
| 8 | THY1.2 | 79.5 |
| 9 | THY1.2 | 88.8 |
| 10 | THY1.2 | 86.4 |

●$5 \times 10^6$ RAMB-treated B10 cells + $15 \times 10^6$ B10.BR cells → B10 host.
$^\Psi$Typing was performed on PBL by one color flow cytometry. Isotype-specific controls were also performed. Chimeras were typed at 6 weeks.

In further studies to characterize the potency of this facilitating effect and estimate the number of cells required for the effect, titration of donor cells was performed to determine the dose at which the facilitating effect was eliminated, as evidenced by mixed chimerism or syngeneic repopulation (see Table 3A). While engraftment of allogeneic bone marrow cells did not occur at all when $5 \times 10^6$ RAMB treated allogeneic bone marrow cells were administered (Table 3A; Groups 1–4), 100% of animals were completely chimeric when $5 \times 10^6$ untreated (Table 3A; Groups 15 and 16) or CD4 depleted (Table 3A Groups 6–8) or CD8 depleted (Table 3A, Groups 9–11), or CD4 + CD8 depleted (Table 3A, Groups 12–14) allogeneic bone marrow cells were administered. Similar results occurred when MAC-1+ cells (Table 3A Group 17) or B220+ cells (Table 3A, Group 19) were removed. Table 3B presents additional data which is cumulative to that presented in Table 3A. These data further support the conclusion that the facilitating cell is a cell separate from the pluripotent hematopoietic stem cell since removal of CD4$^+$ and CD8$^+$ cells would enrich for the stem cell, yet complete allogeneic chimerism began to disappear when <$5 \times 10^6$ allogeneic cells were administered.

TABLE 3A

Titration of Cell Number In Allogeneic Component Of Mixed Bone Marrow Engraftment:
Effect Of Composition On Level Of Chimerism

| Group | Animal No. | Treatment of B10.BR Marrow | % Allogeneic Chimeric Mean (Range) |
|---|---|---|---|
| 1 | 6 | $15 \times 10^6$ RAMB-Treated B10.BR | 17 (2–40) |
| 2 | 5 | $10 \times 10^6$ RAMB-Treated B10.BR | 16 (0–31) |
| 3 | 5 | $5 \times 10^6$ RAMB-Treated B10.BR | 3 (0–8) |
| 4 | 5 | $1 \times 10^6$ RAMB-Treated B10.BR | 0 |
| 5 | 4 | $15 \times 10^6$ Thy1-Depleted B10.BR | 81 (80–83) |
| 6 | 5 | $15 \times 10^6$ CD4-Depleted B10.BR | 97 (96–98) |
| 7 | 5 | $10 \times 10^6$ CD4-Depleted B10.BR | 98 (94–100) |
| 8 | 5 | $5 \times 10^6$ CD4-Depleted B10.BR | 98 (94–99) |
| 9 | 5 | $15 \times 10^6$ CD8-Depleted B10.BR | 100 (99–100) |
| 10 | 5 | $10 \times 10^6$ CD8-Depleted B10.BR | 99 (98–100) |
| 11 | 5 | $5 \times 10^6$ CD8-Depleted B10.BR | 98 (96–100) |
| 12 | 7 | $15 \times 10^6$ CD4 plus CD8 Depleted B10.BR | 98 (96–99) |
| 13 | 7 | $10 \times 10^6$ CD4 plus CD8 Depleted B10.BR | 84 (6–99) |

TABLE 3A-continued

Titration of Cell Number In Allogeneic Component
Of Mixed Bone Marrow Engraftment:
Effect Of Composition On Level Of Chimerism

| Group | Animal No. | Treatment of B10.BR Marrow | % Allogeneic Chimeric Mean (Range) |
|---|---|---|---|
| 14 | 7 | $5 \times 10^6$ CD4 plus CD8 Depleted B10.BR | 81 (0–99) |
| 15 | 4 | $10 \times 10^6$ Untreated B10.BR | 99 (97–99) |
| 16 | 4 | $5 \times 10^6$ Untreated B10.BR | 77 (47–93) |
| 17 | 5 | $15 \times 10^6$ Mac-1-Depleted (Mac-1) | 100 (99–100) |
| 18 | 2 | $15 \times 10^6$ NK-Depleted | 99 (99) |
| 19 | 5 | $15 \times 10^6$ B-Cell-Depleted (B220) | 100 (99–100) |

TABLE 3B

EFFECT OF NEGATIVE SELECTION OF ALLOGENEIC
(B10.BR) CELLULAR SUBSETS ON FACILITATION OF
ENGRAFTMENT OF THE ALLOGENEIC STEM CELL
($5 \times 10^6$ RAMB B10 + $15 \times 10^6$ TREATED B10.BR → B10)

| Group | N | TREATMENT OF ALLOGENIC COMPONENT OF MIXED BONE MARROW INOCULUM | % ALLOGENIC DONOR CHIMERISM: MEAN (RANGE)[1] |
|---|---|---|---|
| 1 | 10 | $15 \times 10^6$ RAMB-Treated | 50 (2–76) |
| 2 | 5 | $10 \times 10^6$ RAMB-Treated | 16 (0–31) |
| 3 | 8 | $5 \times 10^6$ RAMB-Treated | 17 (0–30) |
| 4 | 16 | $15 \times 10^6$ Untreated | 99 (98–100) |
| 5 | 12 | $10 \times 10^6$ Untreated | 99 (97–99) |
| 6 | 12 | $5 \times 10^6$ Untreated | 77 (47–93) |
| 7 | 5 | $15 \times 10^6$ CD4-Depleted | 97 (96–98) |
| 8 | 5 | $10 \times 10^6$ CD4-Depleted | 98 (94–100) |
| 9 | 5 | $5 \times 10^6$ CD4-Depleted | 98 (94–99) |
| 10 | 5 | $15 \times 10^6$ CD8-Depleted | 100 (99–100) |
| 11 | 5 | $10 \times 10^6$ CD8-Depleted | 99 (98–100) |
| 12 | 5 | $5 \times 10^6$ CD8-Depleted | 98 (96–100) |
| 13 | 7 | $15 \times 10^6$ CD4 plus CD8-Depleted | 98 (96–99) |
| 14 | 7 | $10 \times 10^6$ CD4 plus CD8-Depleted | 84 (6–99) |
| 15 | 7 | $5 \times 10^6$ CD4 plus CD8-Depleted | 81 (0–99) |
| 16 | 5 | $15 \times 10^6$ Mac-1-Depleted (Mac-1) | 100 (99–100) |
| 17 | 2 | $15 \times 10^6$ NK-Depleted[2] | 99 (99) |
| 18 | 5 | $15 \times 10^6$ B-Cell-Depleted (B220) | 100 (99–100) |

[1]Typing was performed by flow cytometric analysis on PBL (wide lymphoid gate) using anti-H-2$^b$ and anti-H-2$^k$ mAb at 6 weeks following reconstitution. Some animals were typed a second and third time at later points up to 4 months. As in our previous experience, the percentage of allogeneic chimerism remained stable for individual animals.
[2]All mice received a mixture of $5 \times 10^6$ RAMB-treated syngeneic B10 plus $15 \times 10^6$ variably treated allogenic bone marrow cells ($5 \times 10^6$ RAMB B10 + $15 \times 10^6$ treated B10.BR → B 10) following conditioning with total body irradiation (9.5 Gy) as previously described. Representative summary of negative selection studies performed using monoclonal antibody plus rabbit complement (2 cycles) treatment.

Natural killer (NK) cells have been reported to exert an influence on engraftment of allogeneic bone marrow grfts. These cells express THY1 and NK 1.1 markers in the mouse, NKRP1 in both mice and rats, and CD16 and CD56 in humans. Because anti-NK 1.1 antibody does not fix complement, NK 1.1$^+$ cells were negatively selected using flow cytometry and the remaining NK1.1$^-$ allogeneic bone marrow inoculum utilized as donor cells to prepare mixed allogeneic chimeras. In 4 out of 4 recipients tested that received mixed $5 \times 10^6$ RAMB treated B10 and $5 \times 10^6$ NK 1.1 depleted B10. BR bone marrow, completely allogeneic reconstitution was observed (100% B10. BR), demonstrating that the facilitating cell was not an NK cell.

Similar antibody plus C' depletions were carried out using anti-Class II (I-A$^k$) monoclonal antibody plus complement treatment. However, it is well known that Class II killing by this approach is not as efficient as anti-Class I or subset-directed antibody-mediated cytotoxicity. Table 4 lists the results of one of three experiments performed. These data indicate that Class II depletion using mAb plus C' removed the allogeneic facilitating effect in a manner similar to RAMB. However, because mAb and C' treatment in this instance was not the optimal approach, negative selection experiments using flow cytometry and directly labeled monoclonal antibodies for positive cell sorting were performed as discussed in Section 7, infra.

It has been widely observed that cells that express a cell surface marker at a low density are less likely to be removed by antibody directed against this marker, such as by complement-mediated lysis. This may explain the data regarding the expression of Class II molecules on FC, as well as the disparity in the FC expression of CD8 and CD3 when tested by antibody plus complement as opposed to positive selection by cell sorting using antibodies. Cell sorting is a very precise technique which allows the identification of small populations of cells expressing low levels of certain surface markers. It is highly likely that most FC express CD8, CD3, and Class II at very low levels.

TABLE 4

Effect of Depletion Of Class II$^+$ Cells From Allogeneic
Bone Marrow Inoculum On Level Of
Allogeneic Chimerism

| Mixed Reconstitution ($5 \times 10^6$ RAMB B10 + --) | Animal No. | Repopulation |
|---|---|---|
| 15 x 10$^6$ RAMB B10.BR | 130 | Mixed |
| 15 x 10$^6$ RAMB B10.BR | 131 | Mixed |
| 15 x 10$^6$ RAMB B10.BR | 132 | Mixed |
| 15 x 10$^6$ RAMB B10.BR | 133 | Mixed |
| 15 x 10$^6$ Class II - Depleted B10.BR | 138 | Syngeneic |
| 15 x 10$^6$ Class II - Depleted B10.BR | 139 | Mixed |
| 15 x 10$^6$ Class II - Depleted B10.BR | 140 | Mixed |
| 15 x 10$^6$ Class II - Depleted B10.BR | 141 | Mixed |
| 10 x 10$^6$ Class II - Depleted B10.BR | 142 | Completely Allogeneic |
| 10 x 10$^6$ Class II - Depleted B10.BR | 143 | Syngeneic |
| 10 x 10$^6$ Class II - Depleted B10.BR | 144 | Syngeneic |
| 10 x 10$^6$ Class II - Depleted B10.BR | 145 | Completely Allogeneic |
| 5 x 10$^6$ Class II - Depleted B10.BR | 146 | Syngeneic |
| 5 x 10$^6$ Class II - Depleted B10.BR | 148 | Syngeneic |
| 5 x 10$^6$ Class II - Depleted B10.BR | 149 | Mixed |
| 5 x 10$^6$ Class II - Depleted B10.BR | 150 | Syngeneic |
| 1 x 10$^6$ Class II - Depleted B10.BR | 151 | Mixed |
| 1 x 10$^6$ Class II - Depleted B10.BR | 152 | Mixed |
| 1 x 10$^6$ Class II - Depleted B10.BR | 153 | Mixed |
| 1 x 10$^6$ Class II - Depleted B10.BR | 154 | Mixed |

These data demonstrate that the facilitatory cells are not lysed by antibodies specific for CD4, CD8, a tandem CD4 and CD8, NK1.1, Mac-1 or B220. Therefore, negative selection of cells possessing these markers would remove the GVHD producing cells and enrich for the FC. Following this procedure, at least eighty percent (80%) of total cells would be removed. Negative selection of cells possessing these markers would be a clinically viable approach to preserve and enrich for the FC while eliminating the GVHD-producing cells. Subsequent studies using positive selection demonstrated that the FC are CD8$^+$ (see Section 7, infra). These seemingly contradictory results are probably due to incomplete elimination of CD8$^+$ cells in the negative selection method, i.e., there are not enough CD8 molecules on the surface of the FC for a cytotoxic effect when treated with antibody and complement. Thus, it might not be an ideal approach to use anti-CD8 antibody to remove GVHD-producing cells in an attempt to preserve FC, unless the antibody is first screened for its activity. Moreover, mouse FC were also not removed by anti-CD3 depletion but were shown to be CD3+ by positive cell sorting. The rat FC were not removed by anti-CD3 +C' treatment in rat→mouse bone marrow transplantation. Thus, experimental data disclosed herein show that antibodies specific for MHC Class II antigen, CD8 and CD3 may not completely eliminate FC by complement lysis but such markers are in fact present on the surface of FC when cell sorting and add-back studies are performed.

This observation is particularly important in regard to the expression of CD3 by FC. Since CD3 is a marker that is expressed in high levels by T cells which are the primary GVHD-producing cells, it is possible to use anti-CD3 antibodies to selectively deplete T cells, which preserving FC which express lower levels of CD3. However, in order to use anti-CD3 in this manner, it must be pre-screened in vitro and in vivo for this selective activity prior to its use.

7. EXAMPLE

Addition of Facilitatory Cells Enhances Allogeneic Bone Marrow Engraftment

7.1. Materials and Methods
7.1.1. Positive Selection of FC

Bone marrow was harvested from B10 mouse donor and B10.BR donor in the fashion previously described Example 6, supra. The B10 bone marrow was depleted of T-cells utilizing RAMB and guinea pig complement as previously described. The B10. BR bone marrow was resuspended in Hanks Balanced Salt Solution (HBSS) with 5 ml Hepes (1 molar) per 500 ml at $70 \times 10^6$ cells/ml to which 2% FCS was added. The cells were centrifuged and subsequently fluorescein-conjugated (FITC) anti-Class II monoclonal antibody was added at 1:10 dilution in MEM +FCS to treat $50 \times 10^6$ cells/ml. The cells were incubated for 45 minutes at 4° C., then washed twice at 1000 rpm for 5 minutes in HBSS+2% FCS mixture as sort medium. The cells were then resuspended in medium and filtered through nylon mesh and analyzed by the Fluorescence Activated Cell Sorter (FACS). The dual laser system allowed for 4 fluorescent parameters and two light scatter parameters to be recorded for each analyzed cell. Residual erythrocytes and dual cells and debris were excluded by light scatter and propidium iodide staining. Compensation for spatial overlaps of fluorescein and phycoerythrin, and fluorescein and propidium iodide, was adjusted.

For cell sorting, the stained samples were maintained at 4° C. throughout the sorting procedure. Sorted drops were collected in MEM with 10% FCS. Following isolation of a cell population by FACS, the sample was diluted 1:1 in MEM, centrifuged at 1000 rpm for 10 minutes, the supernatant decanted, and the cell pellet resuspended in 0.5 ml of MEM. The suspension was counted and the concentration adjusted for intravenous injection into lethally irradiated recipients. In these studies, irradiated B10 mice received $5 \times 10^6$ RAMB-treated B10 bone marrow cells+$5 \times 10^6$ RAMB-treated B10. BR bone marrow cells+positively or negatively sorted B10O.BR subsets. Titrations were performed to determine the ratio of syngeneic to allogeneic bone marrow cells in which the majority of recipients would populate as syngeneic or <10% allogeneic. When the ratio of RAMB-treated syngeneic: RAMB-treated allogeneic bone marrow cells was 1:1 ($5 \times 10^6$ RAMB-treated B10+$5 \times 10^6$ RAMB-treated B10. BR→B.10) 57% of the recipients repopulated as syngeneic and the overall mean for allogeneic PBL chimerism was 17%.

7.2. RESULTS

From the negative selection experiments described in Section 6, supra, it was demonstrated that (1) removal of the Class II+ population from the allogeneic bone marrow inoculum removed the facilitating effect, and that (2) administration of the Class II+ population alone did not result in engraftment of allogeneic bone marrow, indicating that the stem cell is not Class II+. In contrast with antibody plus complement depletion of undesired cell types, in which at most 70–80% purity of the facilitatory cell plus stem cell fraction can be obtained, the cell sorter could be used to select fractions containing about 96–99% purity and cell viability of >95%. Data from positive selection and add back studies showed that the facilitatory cell was Class II+ but not Class II bright. Simultaneous morphological studies by electron microscopy identified Class II bright cells as lymphocytes, probably mature B-cells; while the FC exhibited a unique non-lymphoid morphology. (See FIG. 1) Thus, Class II brightness may also be used as a further negative selection marker.

Facilitation of allogeneic stem cell engraftment occurred reliably and reproducibly if Class $II^{dim/intermediate}$, CD45+, CD45R+, or CD8+ donor-specific sorted cells from the intermediate forward scatter and low side scatter ("lymphoid") gate were administered in a recipient (Table 5). However, donor specific Class $II^{dim/intermediate}$ cells from the forward and side light scatter profile which characterized the myeloid gate did not facilitate engraftment, nor did the putative negative fraction. Moreover, MHC-disparate BALB/c (H-$2^d$) third party cells sorted for the same putative markers did not facilitate allogeneic stem cell engraftment in 4 of 4 experiments. On the other hand, CD8+/CD45R+/TCRαβ− FC isolated from H-$2^k$xH-$2^d$ F1 mice were able to enhance the engraftment of RAMB-depleted B10 (H-$2^b$) and B10. BR (H-$2^k$) bone marrow in B10 mice resulting in 100% H-$2^k$ allogeneic chimerism, indicating that haploidentical, i.e. half matched, FC are sufficient to facilitate the engraftment of bone marrow stem cells. Therefore, the FC must be genetically matched, but only partially, to the donor cells.

TABLE 5

Effect of Positive Selection And Add-Back Of Cellular Subsets On Facilitation Of Engraftment: Cell Sorting Experiments
($5 \times 10^6$ RAMB B10 + $5 \times 10^6$ RAMB B10.BR + Sorted Fraction)[1]

| Group | Sorted Fraction | N | Gate[2] | % Allogeneic[3] Chimerism | Sorted Allogeneic[4] Cell Dose × $10^6$ |
|---|---|---|---|---|---|
| A1 | Class II$^{bright}$ | 7 | None | 18 (0–51) | 0.6 (0.1–1.9) |
| A2 | Class II$^{dim,\,intermediate,\,nega\text{-}tive}$ | 7 | None | 99 (98–100) | 12.9 (4–15) |
| B1 | Class II$^{dim,\,intermediate}$ | 3 | None | 94 (89–99) | 2.8 (1.9–3.7) |
| C1 | Class II$^{positive}$ | 2 | Lymphoid | 99 (98–100) | 3.15 (1.6–4.7) |
| C2 | Class II$^{negative}$ | 2 | Lymphoid | 39 (0–75) | 1.4 (0.5–2.3) |
| D1 | Class II$^{dim,\,intermediate}$ | 2 | Lymphoid | 98 | 3.4 (2.7–4.1) |
| D2 | Class II$^{negative}$ | 2 | Lymphoid | 42 (0–85) | 3.45 (1.2–5.7) |
| E1 | Class II$^{positive}$ | 2 | Myeloid | 20 (0–39) | 4.4 (4.5–4.7) |
| E2 | Class II$^{negative}$ | 2 | Myeloid | 25 (2–49) | 0.58 (0.47–0.69) |
| F1 | B220+ | 2 | Lymphoid | 49 | 4.1 |

TABLE 5-continued

Effect of Positive Selection And Add-Back Of Cellular Subsets On Facilitation Of Engraftment: Cell Sorting Experiments (5 × 10⁶ RAMB B10 + 5 × 10⁶ RAMB B10.BR + Sorted Fraction)[1]

| Group | Sorted Fraction | N | Gate[2] | % Allogeneic[3] Chimerism | Sorted Allogeneic[4] Cell Dose × 10⁶ |
|---|---|---|---|---|---|
| F2 | B220⁻ | 2 | Lymphoid | 97 (95–100) | 8.2 (6.3–10) |
| G1 | Mac-1⁺ | 2 | Lymphoid | 35 (23–46) | 3.7 (3.6–3.9) |
| G2 | Mac-1⁻ | 3 | Lymphoid | 99 (98–100) | 6.5 (5.6–8.5) |
| H1 | CD4⁺ | 2 | Lymphoid | 50 (48–52) | 0.29 (0.2–0.36) |
| H2 | CD4⁻ | 2 | Lymphoid | 98 (97–99) | 2.8 (0.62–0.36) |
| I1 | CD8⁺ | 2 | Lymphoid | 97 (95–99) | 0.05 (0.01–0.09) |
| I2 | CD8⁻ | 2 | Lymphoid | 49 (15–83) | 3.8 (3.7–3.9) |
| J1 | CD45⁺ | 3 | Lymphoid | 96 (93–100) | 5.4 (4–8.7) |
| J2 | CD45⁻ | 2 | Lymphoid | 20 (10–13) | 0.45 (0.4–0.5) |
| K1 | CD45R⁺ | 2 | Lymphoid | 97 (96–99) | 2.6 (2.4–2.7) |
| K2 | CD45R⁻ | 2 | Lymphoid | 40 (20–61) | 5.4 (4.4–6.5) |
| Control | No Cells Added | 187 | N/A | 17 (0–30) | None |

[1]All mice were conditioned with Total Body Irradiation (TBI) and received 5 × 10⁶ RAMB-treated B10 + 5 × 10⁶ RAMB-treated B10.BR bone marrow cells plus the positive or negative sorted fraction of bone marrow cell (RAMB B10 + RAMB B10.BR + Sorted Fraction → B10). To control for cell number, controls received a matched number of additional RAMB-treated B10.BR bone marrow cells (5 × 10⁶ RAMB B10 + 5 × 10⁶ RAMB B10.BR + x RAMB B.10BR → B10). A significant facilitating effect did not occur in any of these controls (n = 163). Purity for cell sorting ranged from 87% to 99.1%. Each experiment was repeated at least two times. (N refers to the number of times an experiment was performed.) The sorted cell dose represents the average and range (minimum–maximum) of cells administered in all experiments.
[2]Gate represents the classic forward and side scatter profile of intermediate forward scatter and low side scatter ("lymphoid gate") and high forward and side scatter ("myeloid gate").
[3]Percentage of PBL chimerism was normalized to 100% as previously described. This represents mean (range) of allogeneic chimerism for all experiments performed.
[4]The average and range (minimum–maximum) are represented.

These data indicate that a CD8⁺, CD45⁺, CD45R⁺, Class II$^{dim/intermediate}$, but not Class II$^{bright}$ allogeneic bone marrow cellular population with size and granularity characteristics of the "lymphoid gate" is responsible for facilitating engraftment of the allogeneic stem cell. This could represent a single cell type or a small but heterogeneous cell population. Although the facilitating effect was not removed by depletion of CD8-positive cells using antibody plus complement, the use of the same mAb for cell sorting and add-back experiments revealed that the cell population did indeed express CD8 but was apparently not lysed by antibody plus complement treatment. It is well known in the art that antibody depletion of cells requires the presence of a high density of the corresponding antigen on the cell surface and thus, cells expressing low levels of the antigen may not be eliminated by an antibody effectively, while the same antibody may be used to bind and positively select for the same cell population much more readily.

In order to obtain further purity of the facilitating cell(s) population, two color cell sorting and add-back experiments were performed combining the above putative cell surface markers in various combinations. As in the negative selection and add-back experiments, 5×10⁶ RAMB B10 plus 5×10⁶ RAMB B10.BR bone marrow cells were infused with the putative positive or negatively selected cell population (Table 6). Additional controls prepared which received a matched number of RAMB-treated B10.BR bone marrow cells reliably and reproducibly did not have a facilitating effect (n=196). Using this approach, a cell fraction of purity ranging from 87 to 99% was obtained. The facilitating cell fraction resided in the CD45R⁺ CD8⁺, Class II⁺ CD45⁺, CD8⁺ CD3⁺ fractions in the "lymphoid" gate. In (E) of Table 6, the cells were stained with anti-CD4-FITC plus anti-CD8-FITC, thus, the results included CD4⁺ CD8⁻, CD4⁺ CD8⁺, and CD4⁻ CD8⁺ cells. In several three color sorting studies, the facilitatory cell was shown to be CD8⁺, CD45R⁺ and αβ⁻. As few as 10,000–50,000 sorted cells were sufficient to mediate the facilitating effect. Moreover, the purified fraction of this phenotype was morphologically similar to the Class II$^{dim/intermediate}$ fraction by transmission electron microscopy and by immunocytochemical analysis. These cells display a unique appearance and contain abundant granules filled with granulocyte macrophage colony stimulating factor, IL-3 and IL-4.

TABLE 6

Two and Three Positive Selection Sort and Add-Back Studies to Characterize the Cell Surface Phenotype of the Facilitating Cell

| Group | Sorted Fractions[1] | % Allogeneic Chimerism | # Sorted Cells Added (×10⁶) |
|---|---|---|---|
| A | B220⁻/CD45R⁺ | 99 | 0.54 |
|   | B220⁺/CD45R⁺ | 5 | 2.4 |
| B | CD8⁺/CD45R⁺ | 95 | 0.85 |
|   | CD8⁻/CD45R⁺ | 30 | 3.7 |
| C | CD4⁻/CD45R⁺ | 97 | 5.7 |
|   | CD4⁺/CD45R⁺ | 3 | 0.2 |
| D | THY1.2⁺/CD45R⁺ | 96 | 0.29 |
|   | THY1.2⁻/CD45R⁺ | 77 | 4.2 |
| E[2] | CD4⁺ or CD8⁺ | 99 | 0.05 |
|   | CD4⁻/CD8⁻ | 34 | 4.9 |
| F[3] | CD8⁺/CD45R⁺/TCRαβ⁻ | 100 | 0.0525 |
|   | CD8⁻/CD45R⁺/TCRαβ⁻ | 60 | 1.5 |
| G | CD8⁺/CD3⁺ | 98 | 0.0707 |
|   | CD8⁺/CD3⁻ | 52 | 0.025 |
| H | CD45R⁺/CD8⁺/αβ⁻ TCR⁻ from (k × d) F1 | 99 | — |

[1]The design for this set of experiments is exactly as for Table 5 (5 × 10⁶ RAMB B10 + 5 × 10⁶ RMB B10.BR + sorted fraction → B10). All sorts were performed using the forward and side-scatter properties characteristic of the lymphoid gate. Two fractions were collected: a double positive and a second single positive or negative fraction. Each value represents one recipient. Each experiment was performed at least 2 times. To control for allogeneic cell number, additional controls received a matched number of RAMB-treated B10.BR bone marrow cells. As in Table 5, facilitation of engraftment did not occur in any of these controls.
[2]CD4-FITc and CD8-FITC were utilized for staining. Therefore, the positive fraction could represent cells which were CD4⁺CD8⁺ or CD4⁺CD8⁻ and CD4⁻CD8⁺.
[3]In this 3 color sort, αβ-TCR⁺ cells were excluded, then the following two fractions collected: CD45R⁺ CD8⁺, CD45R⁺ CD8⁻. A total of 4 experiments have yielded similar results.

The facilitating cell and dendritic cells share some phenotypic markers but differ in others. The co-expression of Class II and CD45R on the facilitating cell suggests that these cells may represent a subset of cells of dendritic type lineage.

However, dendritic cells exhibit a classic histologic morphology of elongated interdigitating processes and cell surface phenotype which are clearly distinct from the FC described herein. Further, mature dendritic cells are distinct from FC in being Class II$^{bright}$ and CD8⁻. Most importantly, dendritic cells which are potent antigen presenting cells are not able to facilitate stem cell engraftment. Propagation of mature bone marrow-derived dendritic cells according to the conventional methods (Steinman, 1991, Ann. Rev. Immunol. 9:271) did not facilitate bone marrow stem cell engraftment in the mixed syngeneic/allogeneic model using $5 \times 10^5$ or $1 \times 10^6$ dendritic cells.

The positively sorted Class $II^{dim/intermediate}$ cellular population was analyzed for morphology using transmission electron microscopy (FIG. 1). A very homogeneous population of cells which were approximately 8–10 microns in diameter was present. The cells contained a pericytoplasmic skirt relatively free of granules and a large population of more centrally placed and densely packed granules. The majority of those granules had a dense core reminiscent of platelet alpha granules. The lobed nucleus was indicative of the myeloid lineage but the granules were unlike the homogeneously dense granules of neutrophils or the paracrystalline granules characteristic of eosinophils. The presence of large numbers of highly dense granules and the horseshoe-shaped nucleus makes it highly unlikely that this cell is a T-cell or B-cell population, since lymphoid cells have a rounded nucleus with scant granular cytoplasm and a high nuclear:cytoplasmic ratio. Moreover, the facilitatory cell did not resemble precursor dendritic cells from bone marrow or mature dendritic cells. The sorted Class $II^{bright}$ population exhibited the classic morphology of the mature T/B lymphoid cell population which is clearly distinct from the FC. Because mouse T cells do not express Class $II^{bright}$, the Class II population most likely represents mature B-lymphocytes.

In order to demonstrate that the FC of the invention were not stem cells capable of giving rise to hematopoietic cells and that stem cell engraftment required the presence of FC, purified stem cells and FC were used for allogeneic reconstitution. In this experiment, B10.BR stem cells having a phenotype of Sca $1^+$ and Lin$^-$ (B220$^-$, $\alpha\beta$ TCR$^-$, GR-1$^-$, MAC-1$^-$ and CD8$^-$) were isolated to greater than 95% purity by cell sorting. These cells are believed to be equivalent in biologic function to the CD34$^+$ human stem cells. 50,000 of Sca $1^+$, Lin$^-$ stem cells were injected into irradiated allogeneic B10 mice with or without 50,000 B10. BR FC positively sorted for their dual expression of CD8 and CD45R ($\alpha\beta$-TCR$^-$). Table 7 shows that the stem cells or FC alone did not reconstitute the recipient mice, whereas the combination of FC and stem cells led to allogeneic chimerism. While stem cells alone engrafted in syngeneic recipients due to the presence of endogenous FC, the FC alone did not engraft, further confirming that FC are not stem cells.

TABLE 7

Facilitatory Cells Are Required For
Allogeneic Engraftment of Purified Stem Cells

| Donor Cell Populations (B10.BR) | Recipient | Engraftment |
|---|---|---|
| Sca $1^+$/Lin$^-$ + CD8$^+$/CD45R$^+$/$\alpha\beta$-TCR$^-$ (Stem cells) (FC) | Allogeneic (B10) | + |
| Sca $1^+$/Lin$^-$ (Stem cells) | Allogeneic (B10) | − |
| CD8$^+$/CD45R$^+$ (FC) | Allogeneic (B10) | − |
| Sca $1^+$/Lin$^-$ (Stem cells) | Syngeneic (B10.BR) | + |
| CD8$^+$/CD45R$^+$/$\alpha\beta$-TCR$^-$ (FC) | Syngeneic (B10.BR) | − |

In summary, by using positive selections and add-back experiments, FC were characterized by being THY1$^+$, CD45$^+$, CD45R$^+$, CD3$^+$ Class $II^{dim/intermediate}$ and CD8$^+$. These cells are required for stem cells to engraft in allogeneic and xenogeneic recipients. Morphologically, the cells do not resemble lymphocytes or any other cell types previously described. Thus, the FC are a distinct cellular population that expresses a unique combination of leukocyte markers. It would appear that MHC specific:ligand interaction contributes to the success of the allogeneic engraftment. By contrast, B-cells, macrophage/monocytes, NK cells, CD4$^+$ and Class $II^{bright}$ cells do not exhibit facilitatory activity.

8. EXAMPLE

Depletion of of Specific T Cell Subsets Donor Bone Marrow does not Diminish Allogeneic Cell Engraftment

8.1. Results

Results obtained from studies described in Examples 6 and 7, supra, clearly demonstrate that the FC of the present invention are a distinct cell type from T cells, although certain markers such as Thy-1, CD3, and CD8 are commonly expressed by both cell populations. The recognition that T cells may be selectively and specifically depleted by antibodies to markers only expressed by T cells, and not by FC indicates that TCD of donor bone marrow cells may be used to eliminate GVHD-producing cells without jeopardizing donor cell engraftment in bone marrow transplantation, if the appropriate T cell-specific reagents are used for TCD. In fact, in light of the present invention, findings in the art showing the reduction of donor cell engraftment as a result of TCD using RAMB or anti-Thy-1 antibodies may now be interpreted to mean that those reagents used at the time depleted both T cells and FC.

Table 8 illustrates results of allogeneic bone marrow transplantation performed in rats. Unmodified allogeneic rat bone marrow cells were shown to engraft in allogeneic rats to give rise to mixed chimerism when adoptively transferred with TCD syngeneic rat bone marrow cells. Although this approach was able to establish donor cell engraftment, it has not been a clinically viable protocol because of the high risk of GVHD. On the other hand, TCD of rat donor bone marrow cells with RARB failed to induce engraftment in allogeneic recipients, presumably due to the simultaneous elimination of both FC and GVHD-mediating T cells. However, most importantly, when donor cells were depleted with a T cell-specific reagent such as anti-CD3 or anti-$\alpha\beta$-TCR antibody engraftment of donor cells was established. It should be noted that while FC might be CD3$^+$, certain anti-CD3 antibodies may be able to selectively remove T cells without significantly eliminating FC.

Furthermore, it is well known in the art that lymphohematopoietic chimerism generally correlates with donor-specific tolerance of a recipient. When rats reconstituted with $\alpha$CD3-depleted allogeneic cells were implanted subsequently with heart transplants from the donor rat strain, they were shown to retain the transplants for over 3 months. On the other hand, heart transplants from an irrelevant third party rat strain were rejected by the recipients within about 10 days. Similar results were also observed for skin grafts where donor-specific grafts were accepted and genetically disparate third party grafts were rejected.

Taken together, these results indicate that donor bone marrow cells may be treated with a T cell-specific reagent to deplete only T cells with the retention of FC for use in bone marrow transplantation. This approach eliminates most of the cells responsible for GVHD, without reducing the ability of hematopoietic stem cells to engraft in a recipient. GVHD-producing cells may be further eliminated by treatment of the cellular preparation with antibodies specific for B cells and NK cells. In addition, the engraftment of donor bone marrow cells establishes chimerism in the recipient, inducing a state of donor-specific tolerance in the recipient so as to allow the transplantation of any cell, tissue or organ from the donor to establish long-term or even permanent engraftment. Thus, the presence of FC in a donor cell preparation for bone marrow transplantation may be used as a tolerizing agent without the risk of GVHD to facilitate solid organ transplantation. It should be noted that the induced tolerance is donor specific, thus it would not immunocompromise a recipient's ability to mount an immune response to other antigens.

TABLE 8

Allogeneic Rat Bone Marrow Transplantation

| Treatment of Donor Bone Marrow Cells | Engraftment |
| --- | --- |
| Untreated | + |
| RARB-treated | − |
| anti-CD3 treated | + |

9. EXAMPLE

Facilitatory Cells Enhance Xenogeneic Bone Marrow Engraftment

9.1. Materials and Methods 9.1.1. Xenogeneically Reconstituted Animals (A+B→A)

In mouse+rat→mouse chimeras, mice received $5\times10^6$ T-cell depleted mouse bone marrow cells plus $4\times10^7$ untreated rat bone marrow cells unless otherwise specified. TCD performed with anti-TCR $\alpha\beta$ antibodies and complement, or with antibody-coupled immunomagnetic beads achieved similar results. In mouse→rat chimeras, rats received $250\times10^6$ untreated or treated mouse bone marrow cells.

Under these conditions it has been demonstrated that the majority of rat T-lymphocytes in mouse+rat →mouse chimeras were derived from the rat bone marrow stem cell precursors and not contaminating T-lymphocytes in the bone marrow inoculum, since T-cell maturation proceeded in a developmentally regulated fashion in the thymus. In addition, most T-cells in mouse+rat→mouse chimeras were mouse derived. Radiation controls were prepared to confirm adequacy of the radiation.

9.1.2. Human Marrow Harvest

Human bone marrow was obtained from vertebral bodies from cadaver donors. The vertebral bodies were transported in nutrient rich medium (Ex-Vivo; Whitacker Company) supplemented with 500,000 units of polymyxin, 500,000 unit of bacitracin, and 10% human serum albumin. The vertebral bodies were split into four pieces each. All processing was done at room temperature. The soft cancellous bone was chipped out using rongeurs and the bone marrow cells dislodged by gentle shaking for a total of 90 minutes. At each 30 minute interval, the supernatant was strained through a double layer mesh sieve (pore size 420 microns; 180 microns) and 500 ml of fresh media was added. All fractions were combined, centrifuged at 1000 rpm for 10 minutes, counted, and resuspended to a concentration of $20\times10^6$ cells/ml. With this technique, $40\times10^9$ to $60\times10^9$ cells per 5 vertebral bodies were obtained. Flow cytometry analyses were then performed as described in Example 6, supra, to determine their phenotype.

9.2. Results

The facilitating cell has a similar effect on engraftment of bone marrow across species barriers, for example, rat→mouse, mouse→rat. When $4\times10^6$ rat bone marrow cells and syngeneic mouse cells were transferred into mice after TCD using rabbit-anti-rat brain (RARB) or anti-Thy, lethally irradiated recipients failed to be reconstituted (Table 9). In addition, if rat bone marrow cells were transferred into lethally irradiated mice after TCD using RARB or anti-Thy 1.1 in the absence of syngeneic mouse cells as donor cells, 100% mortality of the recipients resulted due to failure of rescue from radiation-induced aplasia and failure of engraftment (Table 10). This result closely resembles the outcome of human allogeneic bone marrow transplantation, in which TCD of donor cells would generally result in no engraftment and therefore a high mortality rate (up to 70%). On the other hand, if untreated rat bone marrow, or rat bone marrow depleted of $CD4^++CD8^+$ cells or $CD3^+$ cells or $\alpha\beta$-$TCR^+$ cells or $\alpha\beta$-$TCR^+$ cells plus B cells or $\alpha\beta$-$TCR^+$ cells plus NK cells was administered, engraftment was achieved and >90% of recipients survived for more than 180 days. It should be noted that rat FC may be $CD8^+$, similar to the phenotype of the corresponding mouse cells. Thus, the results observed with negative selection using anti-CD8 might, again, be due to their incomplete removal. The FC for xenoengraftment was $\alpha\beta$-$TCR^-$, $CD3^-$ and $CD4^-$ as the facilitating effect was not removed by depleting these cells using immunomagnetic beads or complement-mediated cytotoxicity. Again, the rat FC might also be $CD3^+$ but they were not completely depleted by the antibody.

TABLE 9

Xenogeneic Bone Marrow Transplantation
From Rat into Mouse Recipients (Rat + mouse → Mouse)

| Treatment of Donor Cells | % Rat Chimerism | Tolerance |
| --- | --- | --- |
| untreated | 5–60% | + |
| anti-$\alpha\beta$-TCR | 12–69% | + |
| anti-CD4/CD8 | 52–76% | + |
| anti-Thy 1.1 | no rat cells | − |
| RARB | no rat cells | − |

TABLE 10

Xenogeneic Bone Marrow Transplantation
(Rat → Mouse)

| Treatment of Donor Cells | Outcome |
| --- | --- |
| anti-Thy 1.1 | All dead |
| RARB | All dead |
| anti-$\alpha\beta$-TCR | Engraftment |
| anti-CD4/CD8 | Engraftment |
| anti-CD3 | Engraftment |

It was also observed that animals showing xenogeneic chimerism were tolerant to the donor cells, as measured by a lack of reactivity in mixed-leukocyte reaction as well as acceptance of heart, skin and islet grafts. Therefore, the retention of FC in the donor cell population not only enhanced xenogeneic bone marrow engraftment, it also induced a state of donor-specific tolerance, rendering it possible to perform subsequent or simultaneous xenogeneic cellular or solid organ transplantation from a different species. It is important to note that these tissues function properly in a xenogeneic environment.

A technique has been developed to isolate large numbers of bone marrow cells from human vertebral bodies. Monoclonal antibody staining of the bone marrow was performed using techniques similar to that for rodents to identify corresponding populations of cells. Analyses of the forward scatter and side scatter profile of human bone marrow by FACS identified cells similar in phenotype to FC in rodent bone marrow.

Two color staining was performed to examine whether similar populations of cells were Class II bright, Class II intermediate and dim, B-cell lineage (LEU 12) negative, various CD45 isoforms and T-cell marker negative. In one of these studies, density gradient separation of the bone marrow was utilized prior to the staining to enrich for cell populations of varying density. It was demonstrated that human bone marrow contained a population of Class II positive, B-cell lineage marker negative cells similar to the rodent bone marrow FC. In addition, a Class II bright, B-cell population was also seen.

To determine whether the cell fraction present in human bone marrow which shared cell surface marker similarities with the rodent FC could enhance engraftment of human bone marrow stem cells, a model for mixed xenogeneic chimeras (mouse+human→mouse) was used. Chimeras were prepared in which TCD syngeneic (B10 mouse) plus untreated human ($80 \times 10^6$ cells) were administered to recipients conditioned with 950 rads of total body irradiation. At 1 week following reconstitution, two animals were sacrificed and their bone marrow, spleens, and thymic tissues analyzed for the presence of human cells bearing the cell surface markers HLA-DR (Class II), CD4, CD8, CD19, and CD14. Evidence (<10%) of mixed human chimerism was present in the bone marrow, and <5% chimerism was present in spleens. Animals followed for as long as four months continued to have low but detectable levels of human cells in the bone marrow. The low levels of chimerism observed and the absence of mature human blood cells in mice might be due to the inability of human blood cells to respond to mouse cytokines in the host. Thus, the co-administration of specific growth factors such as interleukin-1 and 3, various colony-stimulating factors, stem cell factor and erythropoietin might be able to support the growth and maturation of human cells in mice. Alternatively, other animal hosts such as baboons which are phylogenetically closer to humans than rodents, have also been used to examine the facilitating function in xenograftment of human bone marrow cells in the presence of the putative FC. Studies involving the transfer of untreated human bone marrow cells ($6 \times 10^8$ cells/kg) into baboons treated with 2200 Rad of radiation showed a low but detectable level of engraftment of human cells of mixed lineages in baboons.

10. EXAMPLE

Mixed Allogeneic Chimerism Prevents Autoimmune Diabetes and Reverses Insulitis

10.1. Materials and Methods
10.1.1. Mouse Autoimmune Model

Non-obese diabetic (NOD) mice were obtained from Taconic Laboratories and housed in a pathogen-free facility at the Pittsburgh Cancer Institute. In the animal facility, female NOD mice developed spontaneous acute onset diabetes at a rate of 65% by six months, and 80% by eight months of age. All animals tested had insulitis by six weeks of age. For establishing mixed allogeneic chimerism, lethally irradiated NOD mice were transplanted with syngeneic bone marrow cells plus allogeneic bone marrow cells from B10. BR or AKR mice. Immunohistochemical analysis of these animals was performed at specific time points following reconstitution.

10.2. Results

The mixed allogeneic chimerism model described herein was used to prevent the development of diabetes in NOD mice. Such mice engrafted with allogeneic bone marrow cells, exhibited mixed allogeneic chimerism up to seven months and the onset of diabetes was prevented in all tested animals. Immunohistochemical analysis of the mice at five months following reconstitution showed that the islets were free of insulitis. In contrast, four of 13 mice reconstituted with only syngeneic bone marrow cells developed acute diabetes and all mice had insulitis. These results suggest that the ability to selectively eliminate T cells responsible for GVHD and preserve FC to enhance allogeneic bone marrow engraftment may allow the extension of bone marrow transplantation to a variety of disease conditions which are not currently amenable to this modality because of GVHD. The co-administration of hematopoietic FC and stem cells may also permit less aggressive cytoreduction of a recipient to allow engraftment. Diseases that can be treated by this modality include, but are not limited to, autoimmunity, immunodeficiency and viral infection such as AIDS.

The present invention is not to be limited in scope by the exemplified embodiments, which are intended as illustrations of individual aspects of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A cellular composition comprising mammalian hematopoietic cells, which are depleted of graft-versus-host-disease-producing cells having a phenotype of $\alpha\beta$ TCR$^+$ and $\gamma\delta$ TCR$^+$, with the retention of mammalian hematopoietic facilitatory cells having a phenotype of CD3$^+$, CD8$^+$, $\alpha\beta$ TCR$^-$ and $\gamma\delta$ TCR$^-$ as determined by antibody staining and flow cytometry, which hematopoietic facilitatory cells are capable of facilitating engraftment of bone marrow cells.

2. The cellular composition of claim 1 in which the hematopoietic facilitatory cells are CD45$^+$.

3. The cellular composition of claim 2 in which the hematopoietic facilitatory cells are CD45R$^+$.

4. The cellular composition of claim 3 in which the hematopoietic facilitatory cells are Thy1$^+$, CD19$^-$ and CD56$^-$.

5. A cellular composition comprising at least about 30% human hematopoietic facilitatory cells having a phenotype of CD3$^+$, CD8$^+$, $\alpha\beta$ TCR$^-$ and $\gamma\delta$ TCR$^-$ as determined by antibody staining and flow cytometry.

6. A cellular composition comprising at least about 95% human hematopoietic facilitatory cells having a phenotype of CD3$^+$, CD8$^+$, $\alpha\beta$ TCR$^-$ and $\gamma\delta$ TCR$^-$ as determined by antibody staining and flow cytometry.

7. The cellular composition of claim 5 or 6 in which the cells are CD45$^+$.

8. The cellular composition of claim 7 in which the cells are CD45R$^+$.

9. The cellular composition of claim 8 in which the cells are Thy1$^+$, CD19$^-$ and CD56$^-$.

10. A cellular composition comprising human hematopoietic cells, which are depleted of graft-versus-host-disease-producing cells having a phenotype of $\alpha\beta$ TCR$^+$ and $\gamma\delta$ TCR$^+$, with the retention of hematopoietic facilitatory cells having a phenotype of CD3$^+$, CD8$^+$, $\alpha\beta$ TCR$^-$ and $\gamma\delta$ TCR$^-$ as determined by antibody staining and flow cytometry, which hematopoietic facilitatory cells are capable of facilitating engraftment of bone marrow cells.

11. The cellular composition of claim 10 in which the hematopoietic facilitatory cells are CD45$^+$.

12. The cellular composition of claim 11 in which the hematopoietic facilitatory cells are CD45R$^+$.

13. The cellular composition of claim 12 in which the hematopoietic facilitatory cells are Thy1$^+$, CD19$^-$ and CD56$^-$.

14. The cellular composition of claim 10 which further comprises CD34$^+$ cells which are histocompatible with the hematopoietic facilitatory cells.

15. The cellular composition of claim 14 in which the depleted graft-versus-host-disease-producing cells further comprise CD19$^+$ and CD56$^+$ cells.

16. A pharmaceutical composition for facilitating hematopoietic CD34$^+$ stem cell engraftment in a recipient, in which the active ingredient is hematopoietic facilitatory cells having a phenotype of CD3$^+$, CD8$^+$, $\alpha\beta$ TCR$^-$ and $\gamma\delta$ TCR$^-$, as determined by antibody staining and flow cytometry, and said hematopoietic facilitatory cells are histocompatible with the CD34$^+$ stem cells.

17. A pharmaceutical composition for bone marrow transplantation in which the active ingredients are CD34$^+$ hematopoietic stem cells and histocompatible hematopoietic facilitatory cells having a phenotype of CD3$^+$, CD8$^+$, $\alpha\beta$ TCR$^-$ and $\gamma\delta$ TCR$^-$, as determined by antibody staining and flow cytometry.

18. A method of partially or completely reconstituting a mammal's lymphohematopoietic system comprising administering to the mammal the pharmaceutical composition of claim 16.

19. A method of partially or completely reconstituting a mammal's lymphohematopoietic system comprising administering to the mammal the pharmaceutical composition of claim 17.

20. The method of claim 18 or 19 in which the mammal is conditioned by total body irradiation.

21. The method of claim 18 or 19 in which the mammal is conditioned by an immunosuppressive agent.

22. The method of claim 18 or 19 in which the mammal is conditioned by a cytoreduction agent.

23. The method of claim 18 or 19 in which the pharmaceutical composition is administered intravenously.

24. The method of claim 18 or 19 in which the mammal is a human.

25. The method of claim 18 or 19 in which the mammal suffers from autoimmunity.

26. The method of claim 25 in which the autoimmunity is diabetes.

27. The method of claim 25 in which the autoimmunity is multiple sclerosis.

28. The method of claim 25 in which the autoimmunity is systemic lupus erythematosus.

29. The method of claim 18 or 19 in which the mammal suffers from immunodeficiency.

30. The method of claim 18 in which the mammal is infected with a human immunodeficiency virus.

31. The method of claim 18 or 19 in which the mammal is infected with a hepatitis virus.

32. The method of claim 18 or 19 in which the mammal suffers from a hematopoietic malignancy.

33. The method of claim 18 or 19 in which the mammal suffers from anemia.

34. The method of claim 18 or 19 in which the mammal suffers from hemoglobinopathies.

35. The method of claim 18 or 19 in which the mammal suffers from an enzyme deficiency state.

36. The method of claim 18 or 19 in which the mammal is human and the pharmaceutical composition is obtained from a human.

37. The method of claim 18 or 19 in which the mammal is human and the pharmaceutical composition is obtained from a non-human animal.

38. The method of claim 37 in which the non-human animal is baboon.

39. A method of inducing donor-specific tolerance in a mammal in order to facilitate long-term engraftment of donor cells, tissues or organs comprising administering to the mammal the pharmaceutical composition of claim 21.

40. A method of inducing donor-specific tolerance in a mammal in order to facilitate long-term engraftment of donor cells, tissues or organs comprising administering to the mammal the pharmaceutical composition of claim 22.

41. The method of claim 39 or 40 in which the donor organ is heart.

42. The method of claim 39 or 40 in which the donor organ is skin.

43. The method of claim 39 or 40 in which the donor organ is liver.

44. The method of claim 39 or 40 in which the donor organ is lung.

45. The method of claim 39 or 40 in which the donor organs are heart and lung.

46. The method of claim 39 or 40 in which the donor organ is kidney.

47. The method of claim 39 or 40 in which the donor tissues are pancreatic islet cells or whole pancreas.

48. The method of claim 39 or 40 in which the donor organ is an endocrine organ.

49. The method of claim 48 in which the endocrine organ is a thyroid gland.

50. The method of claim 48 in which the endocrine organ is a parathyroid gland.

51. The method of claim 48 in which the endocrine organ is a thymus.

52. The method of claim 48 in which the endocrine organ is adrenal cortex.

53. The method of claim 48 in which the endocrine organ is adrenal medulla.

54. The method of claim 39 or 40 in which the donor cells are neurons.

55. The method of claim 39 or 40 in which the donor cells are myocytes.

56. The method of claim 39 or 40 in which the mammal is human and the pharmaceutical composition is obtained from a human.

57. The method of claim 39 or 40 in which the mammal is human and the pharmaceutical composition is obtained from a non-human animal.

58. The method of claim 57 in which the non-human animal is baboon.

59. The method of claim 57 in which the non-human animal is pig.

60. A method for obtaining a cellular composition having at least about 30% mammalian hematopoietic facilitatory cells, comprising subjecting a cell mixture to negative selection to remove cells expressing $\alpha\beta$ TCR, $\gamma\delta$ TCR.

61. A method for obtaining a cellular composition having at least about 95% mammalian hematopoietic facilitatory cells, comprising subjecting a cell mixture to negative selection to remove cells expressing $\alpha\beta$ TCR, $\gamma\delta$ TCR.

62. A method for obtaining a cellular composition depleted of graft-versus-host-disease-producing cells having a phenotype of αβ TCR⁺ and γδ TCR⁺, with the retention of hematopoietic facilitatory cells having a phenotype of $CD3^+$, $CD8^+$, αβ TCR⁻ and γδ TCR⁻, comprising subjecting a cell mixture to negative selection to remove cells expressing αβ TCR and γδ TCR.

63. The method of claim 60, 61 or 62 in which the cells are removed by an antibody.

64. The method of claim 63 in which the antibody is conjugated to a magnetic bead.

65. The method of claim 60, 61 or 62 in which the cellular composition is first separated by density gradient centrifugation to obtain cells in the mononuclear cell fraction.

66. The method of claim 60, 61 or 62 in which the cellular composition is further depleted of cells expressing CD19 and CD56.

67. The method of claim 60, 61 or 62 in which the cellular composition comprises CD34⁺ hematopoietic cells.

68. The method of claim 60, 61 or 62 in which the cellular composition is derived from bone marrow.

69. The method of claim 60, 61 or 62 in which the cellular composition is derived from thymus.

70. The method of claim 60, 61 or 62 in which the cellular composition is derived from peripheral blood.

71. The method of claim 60, 61 or 62 in which the cellular composition is derived from fetal liver.

72. The method of claim 60, 61 or 62 in which the cellular composition is derived from embryonic yolk sac.

* * * * *